United States Patent
Miyake et al.

(10) Patent No.: US 9,253,983 B2
(45) Date of Patent: **\*Feb. 9, 2016**

(54) TRIAZOLE COMPOUND AND USE THEREOF

(75) Inventors: Taiji Miyake, Tokyo (JP); Nobuyuki Araki, Tokyo (JP); Toru Yamazaki, Tokyo (JP)

(73) Assignee: KUREHA CORPORATION, Tokyo (JP)

( \* ) Notice: Subject to any disclaimer, the term of this patent is extended or adjusted under 35 U.S.C. 154(b) by 0 days.

This patent is subject to a terminal disclaimer.

(21) Appl. No.: 14/122,944

(22) PCT Filed: May 30, 2012

(86) PCT No.: PCT/JP2012/063976
§ 371 (c)(1),
(2), (4) Date: Nov. 27, 2013

(87) PCT Pub. No.: WO2012/165499
PCT Pub. Date: Dec. 6, 2012

(65) Prior Publication Data
US 2014/0094362 A1    Apr. 3, 2014

(30) Foreign Application Priority Data

May 31, 2011 (JP) ................................. 2011-122405
May 31, 2011 (JP) ................................. 2011-122409

(51) Int. Cl.
A01N 43/653    (2006.01)
C07B 57/00     (2006.01)
C07D 249/08    (2006.01)

(52) U.S. Cl.
CPC .............. *A01N 43/653* (2013.01); *C07B 57/00* (2013.01); *C07D 249/08* (2013.01)

(58) Field of Classification Search
None
See application file for complete search history.

(56) References Cited

U.S. PATENT DOCUMENTS

| | | |
|---|---|---|
| 4,847,278 A | 7/1989 | Kramer et al. |
| 4,913,727 A | 4/1990 | Stroech et al. |
| 4,921,528 A | 5/1990 | Bockmann et al. |
| 4,938,792 A | 7/1990 | Kumazawa et al. |
| 4,980,488 A | 12/1990 | Stroech et al. |
| 4,988,382 A | 1/1991 | Bockmann et al. |
| 4,988,819 A | 1/1991 | Stroech et al. |
| 4,990,677 A | 2/1991 | Stroech et al. |
| 5,028,254 A | 7/1991 | Kumazawa et al. |
| 5,034,052 A | 7/1991 | Stroech et al. |
| 5,057,532 A | 10/1991 | Seele et al. |
| 5,089,640 A | 2/1992 | Bockmann et al. |
| 5,097,047 A | 3/1992 | Stroech et al. |
| 5,159,118 A | 10/1992 | Kumazawa et al. |
| 5,162,356 A | 11/1992 | Arahira et al. |
| 5,216,006 A | 6/1993 | Scherkenbeck et al. |
| 5,239,089 A | 8/1993 | Kumazawa et al. |
| 5,288,883 A | 2/1994 | Scherkenbeck et al. |
| 5,292,764 A | 3/1994 | Arahira et al. |
| 5,414,105 A | 5/1995 | Kumazawa et al. |
| 5,504,096 A | 4/1996 | Arahira et al. |
| 5,714,507 A | 2/1998 | Valcke et al. |
| 5,804,591 A | 9/1998 | Valcke et al. |
| 6,166,059 A | 12/2000 | Jautelat et al. |
| 8,710,090 B2 \* | 4/2014 | Araki et al. ................... 514/383 |
| 2005/0165076 A1 | 7/2005 | Ammermann et al. |
| 2010/0062938 A1 | 3/2010 | Voeste et al. |
| 2011/0245280 A1 | 10/2011 | Ammermann et al. |
| 2012/0238762 A1 | 9/2012 | Sudo et al. |
| 2014/0113899 A1 \* | 4/2014 | Tateishi et al. ............. 514/239.5 |

FOREIGN PATENT DOCUMENTS

| | | |
|---|---|---|
| CA | 1 171 866 A | 7/1984 |
| DE | 3902031 A1 | 7/1990 |
| EP | 0015756 A1 | 9/1980 |
| EP | 0 047 594 A2 | 3/1982 |

(Continued)

OTHER PUBLICATIONS

Liu, W.; Gan, J; Schlenk, D.; Jury, W. A. "Enantioselectivity in environmental safety of current chiral insecticides." Proceedings of the National Academy of Sciences, 2005, 102, 3, pp. 701-706.\*
Extended European Search Report issued Sep. 29, 2014, in European Patent Application No. 12792524.6.
PCT/ISA/210—International Search Report mailed on Jul. 31, 2012, issued in PCT/JP2012/063976.
PCT/ISA/237—mailed on Jul. 31, 2012, issued in PCT/JP2012/063976.
English translation of International Preliminary Report on Patentability and Written Opinion issued Dec. 12, 2013, in PCT International Application No. PCT/JP2012/063976.

(Continued)

*Primary Examiner* — Mina Haghighatian
*Assistant Examiner* — Erin Hirt
(74) *Attorney, Agent, or Firm* — Birch, Stewart, Kolasch & Birch, LLP

(57) ABSTRACT

In order to provide a compound that shows a strong effect on controlling a plant disease, a triazole compound of the present invention (i) is a compound in which —OH group, —$R^2$ group, and $CH_2$—Ar group are bonded in cis configuration with a cyclopentane, (ii) is (−)-enantiomer or (+) enantiomer, and (iii) is represented by Formula (I):

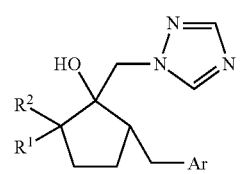

(I)

(wherein $R^1$ represents an alkyl group; $R^2$ represents a haloalkyl group; and Ar represents a substituted/unsubstituted aromatic hydrocarbon group or a substituted/unsubstituted aromatic heterocyclic group.

11 Claims, No Drawings

(56) References Cited

FOREIGN PATENT DOCUMENTS

| | | | |
|---|---|---|---|
| EP | 0 052 424 | A2 | 5/1982 |
| EP | 0 061 835 | A1 | 10/1982 |
| EP | 0 212 605 | A2 | 3/1987 |
| EP | 0 229 642 | A2 | 7/1987 |
| EP | 0267778 | A2 | 5/1988 |
| EP | 0 297 345 | A1 | 1/1989 |
| EP | 0329397 | A1 | 8/1989 |
| EP | 0 488 348 | A1 | 6/1992 |
| EP | 0 951 831 | A1 | 10/1999 |
| EP | 0 970 610 | A1 | 1/2000 |
| GB | 2 064 520 | A | 6/1981 |
| GB | 2 128 605 | A | 5/1984 |
| GB | 2 128 606 | A | 5/1984 |
| GB | 2 129 000 | A | 5/1984 |
| JP | 56-97276 | A | 8/1981 |
| JP | 59-98061 | A | 6/1984 |
| JP | 61-126049 | A | 6/1986 |
| JP | 61-271276 | A | 12/1986 |
| JP | 1-93574 | A | 4/1989 |
| JP | 1-186871 | A | 7/1989 |
| JP | 1-301664 | A | 12/1989 |
| JP | 2-286664 | A | 11/1990 |
| JP | 4-230270 | A | 8/1992 |
| JP | 5-271197 | A | 10/1993 |
| JP | 10-504811 | A | 5/1998 |
| JP | 2000-511891 | A | 9/2000 |
| JP | 2001-302420 | A | 10/2001 |
| JP | 2010-525004 | A | 7/2010 |
| WO | WO 96/01054 | A1 | 1/1996 |
| WO | WO 03/073851 | A1 | 9/2003 |
| WO | WO 2009/135834 | A2 | 11/2009 |
| WO | WO 2010/149414 | A1 | 12/2010 |
| WO | WO 2011/070771 | A1 | 6/2011 |
| WO | WO 2011070742 | A1 | 6/2011 |
| WO | WO 2011070771 | A1 * | 6/2011 ........... C07D 233/60 |

OTHER PUBLICATIONS

Chinese Office Action dated Feb. 12, 2015 for Application No. 201280026419.3 with English language translation.
English translation of International Preliminary Report on Patentability and Written Opinion issued Dec. 27, 2013, in PCT International Application No. PCT/JP2012/064549.
Extended European Search Report issued Oct. 16, 2014, in European Patent Application No. 12796314.8.
International Preliminary Report on Patentability and English translation of the Written Opinion of the International Searching Authority (Forms PCT/IB/338, PCT/IB/373, and PCT/ISA/237), dated Dec. 12, 2013, for International Application No. PCT/JP2012/063976.
International Search Report issued in PCT/JP2012/064549 mailed Aug. 21, 2012.
U.S. Office Action, dated Dec. 18, 2014, for U.S. Appl. No. 14/124,168.
U.S. Office Action dated Jul. 6, 2015 for U.S. Appl. No. 14/124,168.
European Office Action for Application No. 12792524.6 dated Jul. 3, 2015.
Chuman et al., "A Novel Three-Dimensional QSAR Procedure: Varonoi Field Analysis", Quantitative Structure-Activity Relationships (QSAR), vol. 17, Issue 04, 1998, pp. 313-326.
International Search Report Issued in PCT/JP2010/007118, dated Mar. 25, 2011.
Patani et al., "Bioisosterism: A Rational Approach in Drug Design", Chem. Rev., vol. 96, 1996, pp. 3147-3176.
U.S. Notice of Allowance for U.S. Appl. No. 13/508,269 dated Dec. 16, 2013.
U.S. Office Action dated Jun. 3, 2013 for U.S. Appl. No. 13/508,269.
Canadian Office Action for Application No. 2,836,566 dated Feb. 18, 2015.
U.S. Advisory Action for co-pending U.S. Appl. No. 14/124,168, dated Nov. 4, 2015.
Canadian Office Action for Application No. 2,836,566 dated Sep. 1, 2015.
European Office Action for Application No. 12792524.6 dated Nov. 30, 2015.

* cited by examiner

TRIAZOLE COMPOUND AND USE THEREOF

TECHNICAL FIELD

The present invention relates to (i) enantiomers of a triazole compound, (ii) a plant disease controlling agent containing the enantiomers, (iii) a method of controlling plant diseases by use of the plant disease controlling agent, and (iv) use of the enantiomers, and the plant disease controlling agent.

BACKGROUND ART

It is known that certain kinds of 2-substituted-5-benzyl-1-azolylmethylcyclopentanol derivative show an antifungal activity (e.g., see Patent Literatures 1 and 2).

Further, it is reported that some compounds encompassed in 2-(substitution of halogenated hydrocarbon)-5-benzyl-1-azolylmethylcyclopentanol derivative show an anticonvulsive property and an anti-anxiety fighting activity (see Patent Literature 3). Note that Patent Literature 3 does not disclose agro-horticultural agents.

CITATION LIST

Patent Literatures

Patent Literature 1
Japanese Patent Application Publication, Tokukaihei, No. 01-93574 A
Patent Literature 2
Japanese Patent Application Publication, Tokukaihei, No. 01-186871 A
Patent Literature 3
Specification of German Patent Application Publication, No. 3902031
Patent Literature 4
Japanese Patent Application Publication, Tokukaihei, No. 05-271197 A
Patent Literature 5
Japanese Patent Application Publication, Tokukaihei, No. 01-301664 A

SUMMARY OF INVENTION

Technical Problem

Conventionally, there have been demands for a plant disease controlling agent which (i) has low levels of toxicity to humans, (ii) can be handled safely, and (iii) shows a strong effect on controlling a wide range of plant diseases.

The present invention has been made in view of the problem, and it is an object of the present invention to provide a compound that meets the demands.

Solution to Problem

In order to attain the object, the inventors of the present invention conducted an intensive study on a chemical structure and biological activity of a 2-(halogenated hydrocarbon-substituted)-5-benzyl-1-azolylmethylcyclopentanol derivative. As a result, the inventors have found that (i) an azole derivative (specifically, 2-(halogenated hydrocarbon-substituted)-5-benzyl-1-azolylmethylcyclopentanol derivative) represented by the following formula (I) has excellent activity and (ii) each enantiomer of the azole derivative particularly has excellent activity. This led to the realization of the present invention. The present invention is based on such new knowledge, and encompasses the following inventions.

A triazole compound of the present invention in a first aspect is a triazole compound represented by the following formula (I):

[Chem. 1]

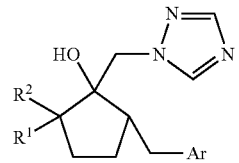

(I)

(wherein $R^1$ represents a $C_1$-$C_6$ alkyl group; $R^2$ represents a $C_1$-$C_6$ haloalkyl group; and Ar represents a $C_6$-$C_{10}$ aromatic hydrocarbon group in which a hydrogen atom(s) may be substituted or a 5-10-membered aromatic heterocyclic group, in which a hydrogen atom(s) may be substituted). The triazole compound is a compound (a) in which —OH group, —$R^2$ group, and $CH_2$—Ar group are bonded in cis configuration with a cyclopentane ring and (b) which is (−)-enantiomer.

A triazole compound of the present invention in a second aspect is a triazole compound represented by the above formula (I), and is a triazole compound (a) in which —OH group, —$R^2$ group, and $CH_2$—Ar group, which are bonded in cis configuration with a cyclopentane ring and (b) which is (+)-enantiomer.

A plant disease controlling agent contains any one of the above triazole compounds.

A method of the present invention is a method of controlling a plant disease, including the step of: carrying out foliage treatment or non-foliage treatment with use of the above plant disease controlling agent.

A seed of the present invention is a seed which has been treated with the above plant disease controlling agent.

Advantageous Effects of Invention

A triazole compound of the present invention has excellent antimicrobial properties against numerous microorganisms that cause plant diseases. Therefore, an agent, which contains the triazole compound of the present invention as an active ingredient, has a strong effect on controlling a wide range of plant diseases.

DESCRIPTION OF EMBODIMENTS

The following description will discuss one embodiment of a triazole compound, a plant disease controlling agent, and a method of controlling plant diseases, all of which are of the present invention.

[Triazole Compound]

The triazole compound in a first aspect is represented by the following formula (I):

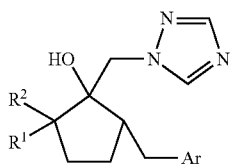

(wherein R¹ represents a $C_1$-$C_6$ alkyl group; R² represents a $C_1$-$C_6$ haloalkyl group; and Ar represents a $C_6$-$C_{10}$ aromatic hydrocarbon group in which a hydrogen atom(s) may be substituted or a 5-10-membered aromatic heterocyclic group, in which a hydrogen atom(s) may be substituted). The triazole compound is a compound (a) in which —OH group, —R² group, and CH₂—Ar group are bonded in cis configuration with a cyclopentane ring and (b) which is (–)-enantiomer (this triazole compound is hereinafter referred to as "compound I (–)").

The triazole compound in a second aspect is represented by the above formula (I), and is a compound (a) in which —OH group, —R² group, and CH₂—Ar group are bonded in cis configuration with a cyclopentane ring and (b) which is (+)-enantiomer (this triazole compound is hereinafter referred to as "compound I(+)").

R¹ represents a $C_1$-$C_6$ alkyl group. Specific examples of the $C_1$-$C_6$ alkyl group encompass methyl group, ethyl group, n-propyl group, isopropyl group, n-butyl group, isobutyl group, sec-butyl group, tert-butyl group, pentyl group, 1-methylbutyl group, 2-methylbutyl group, 1-ethylpropyl group, and hexyl group. Among these, R¹ preferably represents a $C_1$-$C_4$ alkyl group, and more preferably represents a $C_1$-$C_3$ alkyl group.

R² represents a $C_1$-$C_6$ haloalkyl group. Specific examples of a halogen atom contained in R² encompass a fluorine atom, a chlorine atom, a bromine atom, and an iodine atom. Among these, the fluorine atom, the chlorine atom, and the bromine atom are preferable. Note that there are no particular limitations on the number of halogen atoms contained in R².

Specific examples of the $C_1$-$C_6$ haloalkyl group encompass chloromethyl group, dichloromethyl group, trichloromethyl group, 2-chloroethyl group, 1-chloroethyl group, 2,2-dichloroethyl group, 1,2-dichloroethyl group, 2,2,2-trichloroethyl group, 3-chloropropyl group, 2,3-dichloropropyl group, 1-chloro-1-methylethyl group, 2-chloro-1-methylethyl group, 2-chloropropyl group, 4-chlorobutyl group, 5-chloropentyl group, fluoromethyl group, difluoromethyl group, trifluoromethyl group, 2-fluoroethyl group, 1-fluoroethyl group, 2,2-difluoroethyl group, 1,2-difluoroethyl group, 2,2,2-trifluoroethyl group, 3-fluoropropyl group, 2,3-difluoropropyl group, 1-fluoro-1-methylethyl group, 2-fluoro-1-methylethyl group, 2-fluoropropyl group, 3,3,3-trifluoropropyl group, 2,2,3,3-tetrafluoropropyl group, 2,2,3,3,3-pentafluoropropyl group, 4-fluorobutyl group, 5-fluoropentyl group, bromomethyl group, dibromomethyl group, tribromomethyl group, 2-bromoethyl group, 1-bromoethyl group, 2,2-dibromoethyl group, 1,2-dibromoethyl group, 2,2,2-tribromoethyl group, 3-bromopropyl group, 2,3-dibromopropyl group, 1-bromo-1-methylethyl group, 2-bromo-1-methylethyl group, 2-bromopropyl group, 4-bromobutyl group, 5-bromopentyl group, iodomethyl group, diiodomethyl group, 2-iodoethyl group, 1-iodoethyl group, 2,2-diiodoethyl group, 1,2-diiodoethyl group, 2,2,2-triiodoethyl group, 3-iodopropyl group, 2,3-diiodopropyl group, 1-iodo-1-methylethyl group, 2-iodo-1-methylethyl group, 2-iodopropyl group, and 4-iodobutyl group. Among these, R² preferably represents $C_1$-$C_4$ haloalkyl group, and more preferably represents $C_1$-$C_3$ haloalkyl group.

Ar represents a $C_6$-$C_{10}$ aromatic hydrocarbon group in which a hydrogen atom(s) may be substituted or a 5-10-membered aromatic heterocyclic group in which a hydrogen atom(s) may be substituted.

Examples of the $C_6$-$C_{10}$ aromatic hydrocarbon group represented as Ar encompass phenyl group, naphthyl group, indene group, and azulene group. Examples of the 5-10-membered aromatic heterocyclic group represented as Ar encompass thiophene, pyridine, thiazole, furan, pyrrole, oxazole, isoxazole, isothiazole, triazole, furazan, imidazole, pyrazole, pyrazine, pyrimidine, triazine, quinoline, quinoxaline, benzothiophene, benzimidazole, benzothiazole, benzofuran, coumarin, and isoquinoline.

Examples of a substituent, which the aromatic hydrocarbon group/the aromatic heterocyclic group can have, encompass a halogen atom, a phenyl group, a $C_1$-$C_4$ alkyl group, a $C_1$-$C_4$ haloalkyl group, a $C_1$-$C_4$ alkoxy group, and a $C_1$-$C_4$ haloalkoxy group. Examples of the halogen atom encompass a fluorine atom, a chlorine atom, and a bromine atom. Examples of the $C_1$-$C_4$ alkyl group encompass methyl group, ethyl group, n-propyl group, isopropyl group and n-butyl group. Examples of the $C_1$-$C_4$ haloalkyl group encompass trifluoromethyl group, 1,1,2,2,2-pentafluoroethyl group, chloromethyl group, trichloromethyl group, and bromomethyl group. Examples of the $C_1$-$C_4$ alkoxy group encompass methoxy group, ethoxy group, and n-propoxy group. Examples of the $C_1$-$C_4$ haloalkoxy group encompass trifluoromethoxy group, difluoromethoxy group, 1,1,2,2,2-pentafluoroethoxy group, and 2,2,2-trifluoroethoxy group. Note that a hydrogen atom(s) of the phenyl group serving as a substituent may be substituted with a halogen atom.

Note that there are no particular limitations on the number and location of a substituent(s) in the aromatic hydrocarbon group/the aromatic heterocyclic group. Note also that, in a case where there are a plurality of substituents, the substituents may be the same as or different from one another.

An example of Ar can be represented by, but not limited to, the following formulae (a) through (d). Examples of Ar other than those represented by the formulas (a) through (d) are (A) polycyclic aromatic hydrocarbons such as naphthalene and azulene, (B) polycyclic aromatic heterocycle such as quinoline and benzothiophene, and the like.

[Chem. 3]

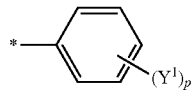

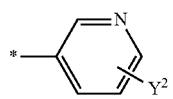

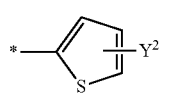

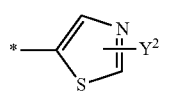

(wherein $Y^1$ represents a halogen atom; a $C_1$-$C_3$ alkyl group, or a $C_1$-$C_3$ haloalkoxy group; p is 0, 1, or 2; $Y^2$ represents a halogen atom, and (iv)* represents bonding with a methylene group).

Compound (I(−)) and Compound (I(+)) are each a compound in which —OH group, —$R^2$ group, and $CH_2$—Ar are bonded in cis configuration with the cyclopentane ring (the groups at position 1 and position 2 of the cyclopentane ring and the groups at position 1 and position 5 of the cyclopentane ring are cis-positioned with respect to one another). Such a compound, in which —OH group, —$R^2$ group, and $CH_2$—Ar group are in cis configuration, has a pair of enantiomers. Of the pair of enantiomers, (i) Compound (I(−)) is (−)-enantiomer and (ii) Compound (I(+)) is (+)-enantiomer. In the present specification, the term "(−)-enantiomer" means an enantiomer that rotates, leftwards, a vibration plane of linearly-polarized light of a sodium D line. On the other hand, the term "(+)-enantiomer" means an enantiomer that rotates, rightwards, a vibration plane of linearly-polarized light of a sodium D line.

Note that, in the present specification, the terms "1,2-cis", "1,5-cis", and "1,2-trans" each refer to (i) —OH group located at position 1 of a cyclopentane ring in a compound represented by the above formula (I), (ii)-$R^2$ group located at position 2 of the cyclopentane ring, (iii) —$CH_2$—Ar group located at position 5 of the cyclopentane ring, or (iv) functional groups corresponding to the —OH group, the —$R^2$ group, and the —$CH_2$—Ar group in an intermediate compound of the compound represented by the above formula (I).

A specific example of Compound (I(−)) is a triazole compound represented by the following formula (Ia):

[Chem. 4]

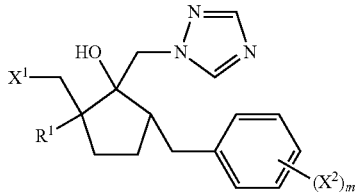

(Ia)

(wherein $R^1$ represents a $C_1$-$C_6$ alkyl group; $X^1$ and $X^2$ independently represent a halogen atom; and m is 0 or 1). The triazole compound is a compound (a) in which —OH group, —$CH_2$—$X^1$ group, and substituted/unsubstituted benzyl group are bonded in cis configuration with a cyclopentane ring and (b) which is (−)-enantiomer.

Likewise, a specific example of Compound (I(+)) is a triazole compound represented by the above formula (Ia). The triazole compound is a compound (a) in which —OH group, —$CH_2$—$X^1$ group, and substituted/unsubstituted benzyl group are bonded in cis configuration with a cyclopentane ring and (b) which is (+)-enantiomer.

$R^1$ in the formula (Ia) is identical to the above-described $R^1$.

$X^1$ and $X^2$ independently represent a halogen atom. Specifically, $X^1$ and $X^2$ independently represent a fluorine atom, a chlorine atom, a bromine atom, or an iodine atom. Among these, (i) $X^1$ preferably represents a fluorine atom, a chlorine atom, or a bromine atom and (ii) $X^2$ preferably represents a fluorine atom or a chlorine atom.

m represents the number of $X^2$ bonded with an aromatic ring of the benzyl group, and is 0 or 1.

In a case where m is 1,4-substituted benzyl group is preferably formed although there are no limitations on a location at which $X^2$ is bonded in the benzyl group.

An even more specific example of Compound (I(−)) is a triazole compound represented by the above formula (Ia), wherein m is 1; and $X^2$ represents a fluorine atom or a chlorine atom. The triazole compound is a compound (a) in which —OH group, —$CH_2$—$X^1$ group, and substituted/unsubstituted benzyl group are bonded in cis configuration with a cyclopentane ring and (b) which is (−)-enantiomer.

Likewise, an even more specific example of Compound (I(+)) is a triazole compound represented by the above formula (Ia), wherein m is 1; and $X^2$ represents a fluorine atom or a chlorine atom. The triazole compound is a compound (a) in which —OH group, —$CH_2$—$X^1$ group, and substituted/unsubstituted benzyl group are bonded in cis configuration with a cyclopentane ring and (b) which is (+)-enantiomer.

Compound (I(−)) and Compound (I(+)) each have excellent antimicrobial properties against numerous microorganisms that cause plant diseases. In addition, adverse effects of Compound (I(−)) on plants are suppressed low.

[Method of Producing Triazole Compound]

(1) Steps Involved in Production

The following description will discuss a method of producing each of Compound (I(−)) and Compound (I(+)). Compound (I(−)) and Compound (I(+)) can each be produced by, for example, the following steps A through E.

(1-1) Step A

Compound (I(−)) and Compound (I(+)) can be obtained by subjecting a racemic mixture (hereinafter referred to as "compound (I')") to preparative separation, which racemic mixture is made up of Compound (I(−)) and Compound (I(+)) that are enantiomers of each other.

An example of a method of separating the enantiomers from each other is a method in which chiral chromatography is employed. Specifically, Compound (I(−)) and Compound (I(+)) can be prepared by being subjected to preparative separation from the compound (I'), which preparative separation is conducted by using, on a stationary phase, one of the following as a mobile phase: hexane/ethanol (100/0 to 0/100), hexane/isopropanol (100/0 to 0/100), ethanol, methanol, and acetonitrile. The stationary phase is prepared by fixing one of the following on a silica gel support: amylose tris(3,5-dimethylphenylcarbamate), cellulose tris(3,5-dimethylphenylcarbamate), cellulose tris(3,5-dichlorophenylcarbamate), amylose tris[(S)-α-methylbenzylcarbamate], cellulose tris (4-methylbenzoate), amylose tris(5-chloro-2-methylphenylcarbamate) and cellulose tris(3-chloro-4-methylphenylcarbamate).

An optical rotation of each of the enantiomers thus separated need only be determined according to a known method.

(1-2) Step B

According to one embodiment of a method of producing Compound (I(−)) and Compound (I(+)), the method includes a step (step B) in which the compound (I') is obtained by substituting, with a halogen atom, a predetermined functional group in a compound represented by the following formula (II) (see the following Reaction Formula (1)). The compound represented by the following formula (II) has a leaving group ($X^3$) on a substituent at position 2 of a cyclopentane ring (hereinafter, the compound represented by the formula (II) is referred to as "Compound (II)"). Note that, in the following, Reaction Formula (1), the compound (I') represented by the formula (Ib) has a structure essentially identical to that of the compound represented by the formula (I).

(Reaction Formula (1))

[Chem. 5]

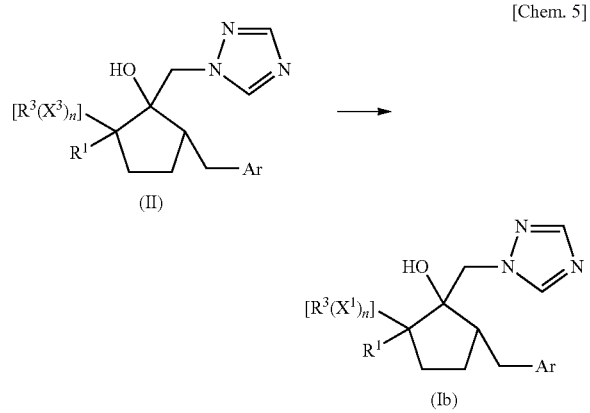

R[1] and Ar in the formula (1) are identical to the above-described R[1] and Ar, respectively.

X[3] represents a leaving group that is substitutable with a halogen atom. Examples of the leaving group encompass substituted sulfonyloxy group and alkoxy group. An example of the substituted sulfonyloxy group is —$OSO_2R^4$. Note that R[4] represents $C_1$-$C_3$ alkyl group, phenyl group, or naphthyl group, in any of which a hydrogen atom can be substituted. Examples of the $C_1$-$C_3$ alkyl group encompass methyl group, ethyl group, n-propyl group, isopropyl group, and trifluoromethyl group. Examples of each of the phenyl group and the naphthyl group encompass 4-methylphenyl group, 2-nitrophenyl group, and 5-dimethylamino naphthyl group. Among these, R[4] preferably represents methyl group and 4-methylphenyl group.

n represents the number of hydrogen atoms that are substitutable with X[3] of R[3]. n is preferably one of 1, 2, 3, 4, and 5, more preferably one of 1, 2, and 3, and most preferably 1.

R[3] represents a $C_1$-$C_6$ alkyl group in which at least one hydrogen atom is substituted with X[3].

X[1] represents a halogen atom, and is identical to the above-described X[1].

Examples of the method for substituting a leaving group with a halogen atom encompass (a) a method according to which a compound having a substituted sulfonyloxy group such as a p-toluenesulfonyloxy group or a methanesulfonyloxy group is substituted with a halogenated salt in a solvent, (b) a method according to which substitution with a hydroxy group or an alkoxy group is carried out by use of hydrochloric acid or hydrobromic acid, (c) a method according to which substitution with a hydroxy group is carried out by use of a halogenated phosphorus, and (d) a method according to which a hydroxy group is reacted with a thionyl halide.

Among the methods (a) through (d), the method (a) is preferred to the others. The following description will discuss the details of the method (a).

A reaction in the method (a) is made normally by mixing, in a solvent, Compound (II) with halogenated acid such as potassium fluoride, cesium fluoride, lithium chloride, potassium chloride, lithium bromide, magnesium bromide, or sodium iodide.

An amount of halogenated acid to be used per mole of Compound (II) is, for example, in the range of 0.1 mole to 100 moles, and preferably in the range of 0.8 mole to 20 moles. A reaction temperature is, for example, in the range of 0° C. to 250° C., and preferably in the range of room temperature to 200° C. Reaction time is, for example, in the range of 0.1 hour to several days, and preferably in the range of 0.2 hour to two days.

(1-3) Step C

Of Compound (II) for use in the step B, a compound, (i) in which the leaving group is a substituted sulfonyloxy group and (ii) which is represented by a formula (IIa) (such a compound is hereinafter referred to as "compound IIa"), can be obtained by taking a step (Step C) in which a compound represented by the following formula (III) (hereinafter referred to as "Compound (III)" is reacted with substituted sulfonyl chloride (see the following Reaction Formula (2)).

[Chem. 6]

(Reaction Formula (2))

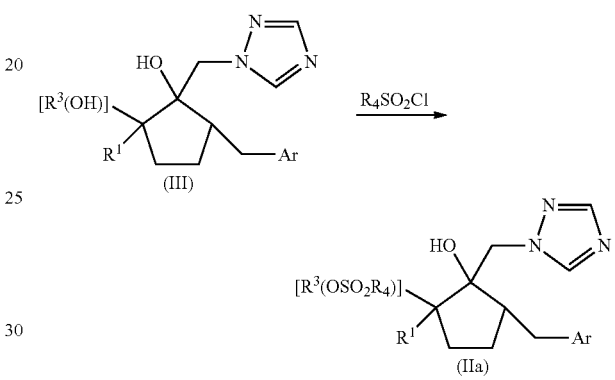

R[4] in the substituted sulfonyl chloride is identical to the above-described R[4].

An amount of the substituted sulfonyl chloride to be used per mole of Compound (III) is, for example, in the range of 0.5 mole to 10 moles, and preferably in the range of 0.8 mole to 5 moles. Although the reaction may proceed without addition of a base, it is preferable to add a base so that hydrogen chloride to be generated by the reaction will be removed. In such a case, an amount of the base to be used per mole of Compound (III) is, for example, in the range of 0 mole to 5 moles (not including 0), and preferably in the range of 0.5 mole to 3 moles.

There are no particular limitations on a kind of base to be used. Examples of the base encompass (i) alkali metal hydrides such as sodium hydride, potassium hydride, and lithium hydride and (ii) organic amines such as triethylamine, pyridine, 4-dimethylaminopyridine, and N,N-dimethylaniline.

A reaction temperature can be appropriately set according to respective types of a solvent and a base to be used. The reaction temperature is preferably in the range of −50° C. to 200° C., and preferably in the range of −20° C. to 150° C. A reaction time can also be appropriately set according to types of a solvent and a base to be used. The reaction time is preferably in the range of 0.1 hour to several days, and more preferably in the range of 0.5 hour to 1 day.

(1-4) Step D

Compound (III) for use in the step (C) can be produced by use of a known method (see, for example, Patent Literature 4). Note, however, that a compound, which (i) has, on position 2 thereof, a hydroxymethyl group and an alkyl group and (ii) is represented by the formula (IIIa) (such a compound is hereinafter referred to as "Compound (IIIa)"), is preferably produced by use of a synthesis method described below.

First, an oxirane derivative represented by the following formula (V) (hereinafter referred to as "Compound (V)") is obtained by converting a carbonyl compound represented by the following formula (VI) (such a carbonyl compound is hereinafter referred to as "compound (VI)") into an oxirane. Then, Compound (V) thus obtained is reacted with 1,2,4-triazole compound represented by the following formula (X) (hereinafter referred to as "Compound (X)") so that a compound represented by the following formula (IV) (hereinafter referred to as "Compound (IV)") is obtained. Then, a protective group of a hydroxy group represented by G is deprotected in Compound (IV) so that Compound (IIIa) is synthesized. The following Reaction Formula (3) represents the series of the reactions involved in this step (Step D):

(Reaction Formula (3))

[Chem. 7]

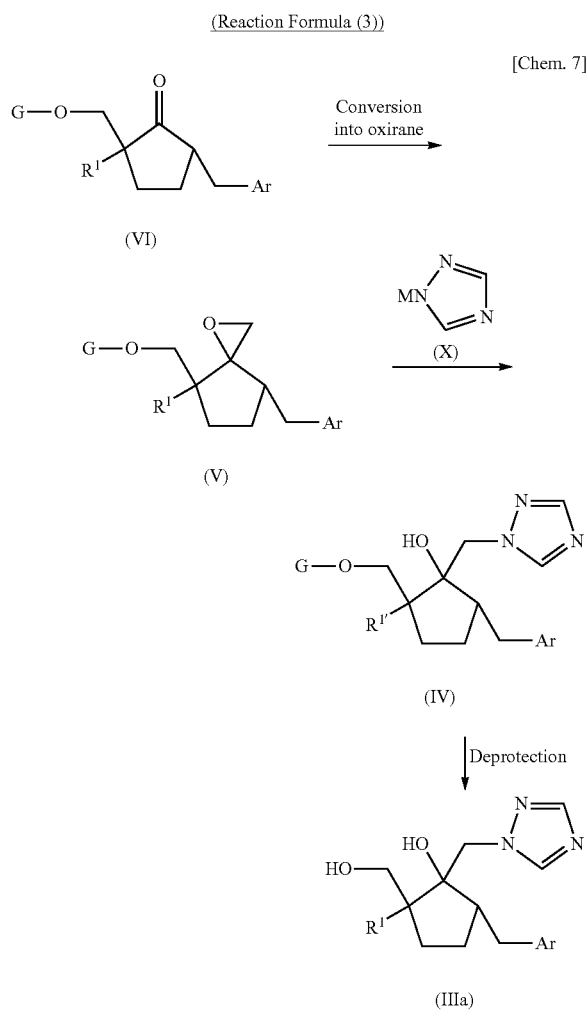

wherein G represents the protective group. Note that the protective group is not limited to any particular one, provided that Compound (IIIa) can be produced from Compound (IV). Examples of the protective group encompass (i) alkoxymethyl groups such as methoxymethyl group and ethoxymethyl group, (ii) lower alkyl groups such as t-butyl group and methyl group, and (iii) substituted/unsubstituted benzyl groups.

According to the formula (X), M represents a hydrogen atom or an alkali metal. The alkali metal is preferably sodium or potassium.

The following description will discuss the sub-steps involved in the step D.

(1-4-1) Sub-Step D1

A first step (sub-step D1) in the step D will be described below. In the sub-step D1, Compound (V) is obtained by converting a compound (VI) into an oxirane.

An example of a first suitable method of synthesizing Compound (V) is a method in which the compound (VI) is reacted with a sulfur ylide in a solvent. Examples of the sulfur ylide encompass (i) sulfonium methylides such as dimethylsulfonium methylide and (ii) sulfoxonium methylides such as dimethylsulfoxonium methylide.

The sulfonium methylide or the sulfoxonium methylide for use in the reaction can be produced by reacting, in a solvent, (i) a sulfonium salt (e.g., trimethylsulfonium iodide, trimethylsulfonium bromide, or the like) or a sulfoxonium salt (e.g., trimethylsulfoxonium iodide, trimethylsulfoxonium bromide, or the like) with (ii) a base.

An amount of the sulfonium methylide or the sulfoxonium methylide per mole of the compound (VI) is preferably in the range of 0.5 mole to 5 moles, and more preferably in the range of 0.8 mole to 2 moles.

The solvent for use in the reaction is not limited to any particular one. Examples of the solvent encompass (i) amides such as dimethyl sulfoxide, N-methylpyrrolidone and N,N-dimethylformamide, (ii) ethers such as tetrahydrofuran and dioxane, and (iii) a mixture of any of the above.

The base for use in the production of the sulfonium methylide or the sulfoxonium methylide is not limited to any particular one. Examples of the base encompass (i) metal hydrides such as sodium hydride and (ii) alkoxide of alkali metals such as sodium methoxide, sodium ethoxide, sodium t-butoxide, and potassium t-butoxide.

A reaction temperature and a reaction time can each be appropriately set according to respective types of (a) the solvent, (b) the compound (VI), (c) the sulfonium salt or the sulfoxonium salt, (d) the base, and the like. The reaction temperature is preferably in the range of −100° C. to 200° C., and more preferably in the range of −50° C. to 150° C. The reaction time is preferably in the range of 0.1 hour to several days, and more preferably in the range of 0.5 hour to two days.

An example of a second synthesis method of synthesizing Compound (V) is a method in which (a) the compound (VI) is reacted with samarium iodide and diiodomethane, and then (b) a compound obtained by the reaction is processed with the use of a base. Such a method will be described below.

The base for use in the second synthesis method is not limited to any particular one. For example, sodium hydroxide or the like can be used as the base. An amount of the base to be used per mole of the compound (VI) is not particularly limited, but is preferably in the range of 0.5 mole to 10 moles, and more preferably in the range of 0.8 mole to 6 moles, for example. Further, in the case where the compound thus reacted is processed with a base, a sodium hydroxide aqueous solution or the like may be used since no anhydrous system is required.

The samarium iodide for use in the second synthesis method can be produced by reacting, in an anhydrous solvent, (i) metal samarium with (ii) 1,2-diiodoethane or diiodomethane.

Examples of the solvent for use in the second synthesis method encompass, but are not limited to, ethers such as tetrahydrofuran.

A reaction temperature and a reaction time can each be appropriately set according to respective types of the solvent, the compound (VI), the base, and the like. The reaction temperature is preferably in the range of −100° C. to 150° C., and more preferably in the range of −50° C. to 100° C. The reaction time is preferably in the range of 0.1 hour to several days, and more preferably in the range of 0.5 hour to two days.

(1-4-2) Sub-Step D2

A next step (Sub-step D2) in the step D will be described below. In the sub-step D2, Compound (IV) is obtained by reacting Compound (V) with Compound (X).

Compound (IV) is produced as follows: Compound (V) and Compound (X) are mixed together, so that a carbon-nitrogen bond is formed between (i) a carbon atom constituting an oxirane ring in an oxirane derivative (the compound (V)) and (ii) a nitrogen atom in 1,2,4-triazole.

Examples of the solvent encompass, but are not limited to, amides such as N-methylpyrrolidone and N,N-dimethylformamide.

An amount of Compound (X) to be used per mole of Compound (V) is, for example, in the range of 0.5 mole to 10 moles, and preferably in the range of 0.8 mole to 5 moles. Note that, as desired, a base can be added to the mixture of Compound (V) and Compound (X). In such a case, an amount of the base to be used per mole of Compound (X) is, for example, in the range of 0 mole to 5 moles (not including 0), and preferably in the range of 0.5 mole to 2 moles.

A reaction temperature can be appropriately set according to respective types of the solvent, the base, and the like. The reaction temperature is preferably in the range of 0° C. to 250° C., and more preferably in the range of 10° C. to 150° C. A reaction time can also be appropriately set according to respective types of the solvent, the base, and the like. The reaction time is preferably in the range of 0.1 hour to several days, and more preferably in the range of 0.5 hour to two days.

It is possible to produce Compound (IV) by (i) producing compound (V) and then (ii) causing Compound (V), which has been thus produced, to react with Compound (X) in stages. Note, however, that, in a case where a conversion of Compound (VI) into an oxirane is solely carried out in the first method of synthesizing Compound (V), it may cause a reduction in yield by producing a by-product such as an oxetane derivative. In order to avoid the reduction in yield, it is only necessary to convert Compound (V) into an azole while Compound (V) is being produced.

[Chem. 8]

(Reaction Formula (4))

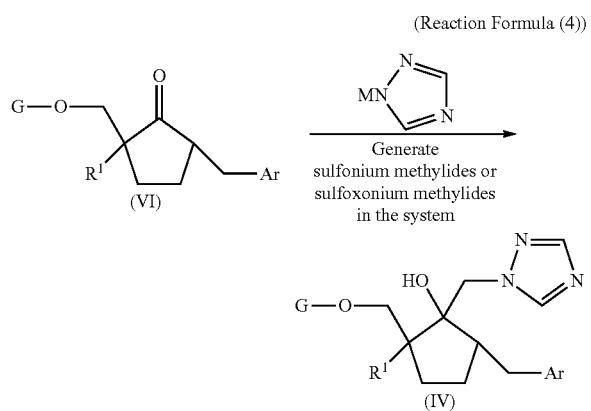

In such a case, Compound (VI) and Compound (X) are dissolved in a solvent. To this, additions are then intermittently made, which additions are (a) a sulfonium salt such as a trimethylsulfonium salt or a sulfoxonium salt such as a trimethylsulfoxonium salt and (b) a base. This causes sulfonium methylide such as dimethylsulfonium methylide or sulfoxonium methylide such as dimethyl sulfoxonium methylide to be produced in the reaction system. In this way, the production of Compound (V) and the conversion thereof into an azole are carried out simultaneously.

The solvent for use in the above process is not limited to any particular one. Examples of the solvent encompass (i) polar solvents having an amide bond, such as N-methylpyrrolidone and N,N-dimethylformamide, (ii) dimethyl sulfoxide, and (iii) a mixture of a polar solvent and alcohol. An example of the alcohol is t-butanol.

The base for use in the production of the sulfonium methylides and the sulfoxonium methylides is not limited to any particular one. Examples of the base encompass (i) a metal hydride such as sodium hydride and (ii) an alkoxide of an alkali metal such as sodium methoxide, sodium ethoxide, sodium t-butoxide, and potassium t-butoxide. In addition, an alkali metal salt of 1,2,4-triazole can also be used.

A reaction temperature can be appropriately set according to respective types of (a) the solvent, (b) Compound (VI), (c) the sulfonium salt or the sulfoxonium salt, (d) the base, and the like. A reaction temperature is preferably in the range of −100° C. to 250° C., and more preferably in the range of −50° C. to 200° C. A reaction time can also be appropriately set according to (a) the solvent, (b) Compound (VI), (c) the sulfonium salt or the sulfoxonium salt, (d) the base, and the like. The reaction time is preferably in the range of 0.1 hour to several days, and more preferably in the range of 0.5 hour to two days.

Provided that desired results can be achieved, there are no particular limitations on the number of times the additions ((a) the sulfonium salt such as a trimethylsulfonium salt or the sulfoxonium salt such as a trimethylsulfoxonium salt and (b) the base) are intermittently made. For example, each of the additions can be made preferably 2 times to 20 times, and more preferably 3 times to 15 times. A total amount of the sulfonium salt such as a trimethylsulfonium salt or the sulfoxonium salt such as a trimethylsulfoxonium salt to be used per mole of Compound (VI) is preferably in the range of 0.5 mole to 5 moles, and more preferably in the range of 0.8 mole to 2 moles.

An amount of Compound (X) per mole of Compound (VI) is, for example, in the range of 0.5 mole to 10 moles, and more preferably in the range of 0.8 mole to 5 moles. Compound (X) is preferably one wherein M is an alkali metal.

Note that reference may be made to Patent Literature 5 for the details of steps involved in a method in which an oxirane derivative is produced and converted into an azole simultaneously, which method is to be employed in production of an azolylmethylcycloalkanol derivative.

(1-4-3) Sub-Step D3

A next step (Sub-step D3) in the step D will be described below. In the sub-step D3, Compound (IIIa) is obtained by deprotecting a protective group of Compound (IV).

Note that desired conditions, under which to deprotect the protective group, vary, depending on a kind of the protective group. In a case where the protective group is (i) an alkoxymethyl group such as a methoxymethyl group and an ethoxymethyl group or (ii) a lower alkyl group such as a t-butyl group and a methyl group, it is preferable to deprotect the protective group (a) in a solvent and (b) under acidic conditions such as conditions in which hydrogen chloride, sulfuric acid, or the like is employed.

Preferable examples of the acid to be used encompass (i) a halogenated hydrogen such as hydrogen chloride and (ii) an inorganic acid such as sulfuric acid. An amount of the acid to be used per mole of Compound (IV) is, for example, in the range of 0.5 mole to 100 moles, and preferably in the range of 0.8 mole to 20 moles, although the amount is not particularly limited to these.

A reaction temperature is, for example, in the range of 0° C. to 200° C., and preferably in the range of room temperature to 100° C. A reaction time is, for example, in the range of 0.1 hour to several days, and more preferably in the range of 0.5 hour to two days.

(1-5) Step E

Compound (VI) for use in the step D can be synthesized by the following method:

First, a compound represented by the following formula (VIII) (such a compound is hereinafter referred to as "Compound (VIII)") is obtained by hydroxymethylating a keto ester compound represented by the following general formula (IX) (such a compound is hereinafter referred to as "Compound (IX)"). Then, Compound (VIII) thus obtained is led to conversion into a compound represented by the following formula (VII) (such a compound is hereinafter referred to as "Compound (VII)") by introducing a protective group such as a methoxymethyl group or a t-butyl group to a hydroxy group of Compound (VIII). Then, a carbonyl compound represented by the following formula (VI) (i.e., Compound (VI)) is obtained by subjecting Compound (VII) to hydrolysis and decarbonation. The following Reaction Formula (5) represents the series of these reactions involved in the step E:

[Chem. 9]

(Reaction Formula (5))

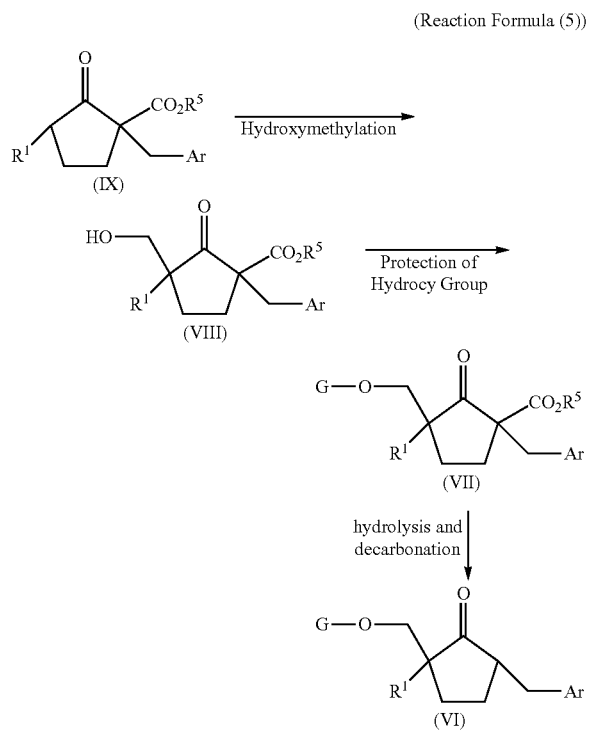

Wherein $R^5$ represents a $C_1$-$C_4$ alkyl group. Examples of the $C_1$-$C_4$ alkyl group encompass methyl group, ethyl group, isopropyl group, n-propyl group, 1-methylpropyl group, 2-methylpropyl group, and n-butyl group.

The following description will discuss the sub-steps involved in the step E.

(1-5-1) Sub-Step E1

In the sub-step E1 in the step E, Compound (VIII) is obtained by hydroxymethylating Compound (IX). The sub-step E1 can be carried out by use of a method in which Compound (IX) is reacted with formaldehyde in a solvent and in the presence of a base.

An amount of the formaldehyde to be used per mole of Compound (IX) is, for example, in the range of 0.5 mole to 20 moles, and preferably in the range of 0.8 mole to 10 moles.

Examples of the base encompass, but are not limited to, (i) carbonates of an alkali metal such as sodium carbonate and potassium carbonate and (ii) hydroxides of an alkali metal such as sodium hydroxide. An amount of the base per mole of Compound (IX) is, for example, in the range of 0.1 mole to 10 moles, and preferably in the range of 0.2 mole to 5 moles.

A reaction temperature is, for example, in the range of 0° C. to 250° C., and preferably in the range of 0° C. to 100° C. A reaction time is, for example, in the range of 0.1 hour to several days, and preferably in the range of 0.5 hour to two days.

Note that Compound (IX) used in the sub-step E1 need only be produced by use of a known method (e.g., the method disclosed in Patent Literature 1).

(1-5-2) Sub-Step E2

A next step (sub-step E2) in the step E will be described below. In the sub-step E2, Compound (VII) is obtained by introducing a protective group to a hydroxy group of Compound (VIII).

Preferable examples of the protective group for protecting the hydroxy group encompass, but are not limited to, (i) alkoxymethyl groups such as a methoxymethyl group and an ethoxymethyl group and (ii) lower alkyl groups such as a t-butyl group. The introduction of the protective group is carried out under acidic catalytic conditions. In a case (case (a)) where the protective group is an alkoxymethyl group, it is preferable to adopt a method employing acetal exchange of the hydroxy group of Compound (VIII) and a formaldehyde dialkyl acetal. In a case (case (b)) where the protective group is a t-butyl group, it is preferable to adopt a method in which the hydroxy group of Compound (VIII) is added to isobutene.

First, the case (a) will be described below.

Examples of an acid encompass (i) inorganic acids such as hydrochloric acid, phosphoric acid (including a compound, such as diphosphorus pentoxide, that allows an acidic group to be produced by addition of alcohol and water), and sulfuric acid and (ii) organic acids such as p-toluenesulfonic acid. The formaldehyde dialkyl acetal is preferably employed in the presence of such as acid and in a solvent or in a solvent-free system. It is more preferable to add a compound, such as diphosphorus pentoxide, that is capable of removing alcohol produced.

An amount of the formaldehyde dialkyl acetal to be used per mole of Compound (VIII) is, for example, in the range of 0.5 mole to 50 moles, and preferably in the range of 0.8 mole to 10 moles. An amount of the acid to be used per mole of Compound (VIII) is, for example, 0.01 mole to 10 moles, and preferably in the range of 0.05 mole to 5 moles.

A reaction temperature is, for example, in the range of 0° C. to 250° C., and preferably in the range of 0° C. to 150° C. A reaction time is, for example, in the range of 0.1 hour to several days, and preferably in the range of 0.5 hour to two days.

In the case (b), it is preferable to cause Compound (VIII) to react with isobutene in a solvent and in the presence of (A) an inorganic acid such as hydrochloric acid, phosphoric acid, or sulfuric acid or (B) an organic acid such as toluenesulfonic acid or trifluoroacetic acid.

An amount of the isobutene to be used per mole of Compound (VIII) is, for example, in the range of 0.5 mole to 100 moles, and preferably in the range of 0.8 mole to 20 moles. An amount of the acid to be used per mole of Compound (VIII) is, for example, in the range of 0.01 mole to 10 moles, and preferably in the range of 0.05 mole to 5 moles.

A reaction temperature is, for example, in the range of 0° C. to 200° C., and preferably in the range of 0° C. to 100° C. A reaction time is, for example, in the range of 0.1 hour to several days, and preferably in the range of 0.5 hour to two days.

(1-5-3) Sub-Step E3

A next step (sub-step E3) in the step E will be described below. In the sub-step E3, Compound (VI) is obtained by subjecting Compound (VII) to hydrolysis and decarbonation.

It is preferable to carry out such reactions in a solvent and in the presence of a base. Preferable examples of the base encompass alkali metal bases such as sodium hydroxide and potassium hydroxide. An amount of the base to be used per mole of Compound (VII) is, for example, in the range of 0.1 mole to 50 moles, and preferably in the range of 0.2 mole to 20 moles.

Examples of the solvent encompass (i) water, (ii) water combined with, for example, an alcohol, and (iii) a solvent composition consisting of solvents (such as water and toluene) which do not form a homogenous layer (in this case, it may be preferable to use a phase transfer catalyst (e.g., a customary quaternary ammonium salt) in the reaction system).

A reaction temperature is, for example, in the range of 0° C. to a reflux temperature, and preferably in the range of room temperature to a reflux temperature. A reaction time is, for example, in the range of 0.1 hour to several days, and preferably, in the range of 0.5 hour to 24 hours.

Note that, unless specified otherwise, examples of the solvent, the base, the acid, and the like to be used in each of the steps above of the production method are as follows:

(2) Solvents

A solvent used in the production method is not particularly limited, provided that the solvent is not involved in the reaction. Examples of the solvent generally include: ethers such as diethyl ether, tetrahydrofuran, and dioxane; alcohols such as methanol, ethanol, and isopropanol; aromatic hydrocarbons such as benzene, toluene, and xylene; aliphatic hydrocarbons such as petroleum ether, hexane, and methylcyclohexane; and amides such as N,N-dimethylformamide, N,N-dimethylacetamide, and N-methyl-2-pyrrolidinone. Other examples of the solvent include water, acetonitrile, ethyl acetate, acetic anhydride, acetic acid, pyridine, and dimethyl sulfoxide. Two or more of these solvents may be used in combination.

Alternatively, the solvent may be a solvent composition composed of solvents which do not form a homogenous layer with each other. In this case, a phase-transfer catalyst such as a general-use quaternary ammonium salt or a crown ether may be added to the reaction system.

(3) Bases and Acids

The solvent described above may contain a base or an acid.

A base is not particularly limited. Examples of the base include: alkali metal carbonates such as sodium carbonate, sodium hydrogen carbonate, potassium carbonate, and potassium hydrogen carbonate; alkaline earth metal carbonates such as calcium carbonate and barium carbonate; alkali metal hydroxides such as sodium hydroxide and potassium hydroxide; alkali metals such as lithium, sodium, and potassium; alkali metal alkoxides such as sodium methoxide, sodium ethoxide, and potassium t-butoxide; alkali metal hydrides such as sodium hydride, potassium hydride, and lithium hydride; alkali metal organometallic compounds such as n-butyl lithium; alkali metal amides such as lithium diisopropyl amide; and organic amines such as triethylamine, pyridine, 4-dimethylaminopyridine, N,N-dimethylaniline, and 1,8-diazabicyclo-7-[5.4.0]undecene.

An acid is not particularly limited. Examples of the acid include: inorganic acids such as hydrochloric acid, hydrobromic acid, hydroiodic acid, and sulfuric acid; organic acids such as formic acid, acetic acid, butyric acid, trifluoroacetic acid, and p-toluenesulfonic acid; and Lewis acids such as lithium chloride, lithium bromide, rhodium chloride, aluminum chloride, and boron trifluoride.

[Plant Disease Controlling Agent and Method of Controlling Plant Diseases]

The following description will discuss (i) the usefulness of triazole compounds (Compound (I(−)) and Compound (I(+))) of the present invention as plant disease controlling agents and (ii) a method of controlling plant diseases with the use of the triazole compounds.

Compound (I(−)) and Compound (I(+)) each contain a 1,2,4-triazolyl group, and therefore forms an acid salt or a metal complex with an inorganic acid or an organic acid. Compound (I(−)) and Compound (I(+)) each in the form of such an acid salt or a metal complex may also be used.

(1) Plant Diseases Control Effect

The following description will discuss the usefulness of a plant disease controlling agent of the present invention. Compound (I(−)) and Compound (I(+)) each control a wide variety of plant diseases including foliage diseases, seed-borne diseases and soil-borne diseases. Examples of diseases to be treated with the plant disease controlling agent include: soybean rust (*Phakopsora pachyrhizi*, *Phakopsora meibomiae*); rice blast (*Pyricularia grisea*, *Pyricularia oryzae*); rice brown spot (*Cochliobolus miyabeanus*); rice sheath blight (*Rhizoctonia solani*); apple powdery mildew (*Podosphaera leucotricha*); apple scab (*Venturia inaequalis*); apple blossom blight (*Monilinia mali*); apple *alternaria* blotch (*Alternaria alternata*); apple *valsa* canker (*Valsa malia*); pear black spot (*Alternaria kikuchiana*); pear powdery mildew (*Phyllactinia pyri*); pear rust (*Gymno sporangium asiaticum*); pear scab (*Venturia nashicola*); grape powdery mildew (*Uncinula necator*); grape downy mildew (*Plasmopara viticola*); grape ripe rot (anthracnose) (*Glomerella cingulata*); barley powdery mildew (*Erysiphe graminis* f. sp *hordei*); barley stem rust (*Puccinia graminis*); barley stripe rust (*Puccinia striiformis*); barley stripe (*Pyrenophora graminea*); barley scald (*Rhynchosporium secalis*); barley loose smut (*Ustilago nuda*); wheat powdery mildew (*Erysiphe graminis* f. sp *tritici*); wheat brown rust (*Puccinia recondita*); wheat stripe rust (*Puccinia striiformis*); wheat eye spot (*Pseudocercosporella herpotrichoides*); wheat *Fusarium* head blight (*Fusarium graminearum*); wheat pink snow mold (*Microdochium nivale*); wheat take-all disease (*Gaeumannomyces graminis*); wheat glume blotch (*Phaeosphaeria nodorum*); wheat leaf blight (*Septoria tritici*); cucurbit powdery mildew (*Sphaerotheca fuliginea*); cucurbit anthracnose (*Colletotrichum lagenarium*); cucumber downy mildew (*Pseudoperonospora cubensis*); cucumber *phytophthora* rot (*Phytophthora capsici*); tomato powdery mildew (*Erysiphe cichoracearum*); tomato early blight (*Alternaria solani*); eggplant powdery mildew (*Erysiphe cichoracearum*); strawberry powdery mildew (*Sphaerotheca humuli*); tobacco powdery mildew (*Erysiphe cichoracearum*); sugar beet *cercpspora* leaf spot (*Cercospora beticola*); plum brown rot (*Monilinia fructicola*); various-plants-affecting gray mold (*Botrytis cinerea*); *sclerotinia* rot (*Sclerotinia sclerotiorum*); grape rust (*Phakopsora ampelopsidis*); tobacco brown spot (*Alternaria longipes*); potato early blight (*Alternaria solani*); soybean brown spot (*Septoria glycines*); soybean purple stain (*Cer-

*cospora kikuchii*); rice leaf blight (*Xanthomonas oryzae*); rice stem rot (*Helminthosporium sigmoideun*); rice Bakanae disease (*Gibberella fujikuroi*); rice damping-off (*Pythium aphanidermatum, Rhizopus oryzae*); corn smut (*Ustillaga maydis*); watermelon *fusarium* wilt (*Fusarium oxysporum* f. sp. *niveum*); cucumber *fusarium* wilt (*Fusarim oxysporum* f. sp. *cucumerinum*); blue mold of citrus fruits (*Penicillium italicum*); and white radish yellow (*Fusarium oxysporum* f. sp. *raphani*).

Examples of plants to be treated with the plant disease controlling agent include: wild plants; cultivated plants; plants and cultivated plants obtained by conventional plant breeding methods such as crossbreeding and protoplast fusion; and transgenic plants and cultivated plants obtained by genetic engineering. Examples of the transgenic plants and cultivated plants include herbicide-resistant crops, insect-resistant crops in which a gene which produces a insecticidal protein is introduced, disease-resistant crops in which a gene which produces a disease resistance inducer is introduced, crops with improved taste, crops with improved productivity, crops with better keeping quality, and crops with improved yield. Specific examples of the transgenic cultivated plants include ROUNDUP READY, LIBERTY LINK, CLEARFIELD, YIELDGARD, HERCULEX, and BOLLGARD, all of which are registered trademarks.

(2) Plant Growth Promoting Effect

Furthermore, each of Compound (I(-)) and Compound (I(+)) is also effective in controlling the growth of a wide variety of crop plants and horticultural plants to thereby increase the yield or quality of the plants. Examples of such plants include: wheat; barley; oats; rice; rapeseed; sugarcane; corn; maize; soybean; pea; peanut; sugar beet: cabbage; garlic; radish; carrot; apple; pear; citric fruits such as mandarin, orange, and lemon; peach; cherry; avocado; mango; papaya; red pepper; cucumber; melon; strawberry; tobacco; tomato; eggplant; lawn grass; chrysanthemum; azalea; and other ornamental plants.

(3) Formulations

A plant disease controlling agent containing Compound (I(-)) or Compound (I(+)) as an active ingredient is usually used in the form of a formulation such as dust, wettable powder, granules or emulsifiable concentrate. The formulation is a mixture of (i) the plant disease controlling agent (ii) and a solid carrier, a liquid carrier, a surfactant and/or some other formulation auxiliary agent.

It is only necessary that such a formulation contain, as an active ingredient, Compound (I(-)) or Compound (I(+)) in an amount of 0.1 wt % to 95 wt %, preferably 0.5 wt % to 90 wt %, and more preferably 2 wt % to 80 wt %.

Examples of carriers, diluents and surfactants serving as the formulation auxiliary agents are as follows. Examples of the solid carrier include talc, kaolin, bentonite, diatomaceous earth, white carbon, and clay. Examples of a liquid diluent include water, xylene, toluene, chlorobenzene, cyclohexane, cyclohexanone, dimethyl sulfoxide, dimethylformamide, and alcohols. The surfactant may be selected as appropriate according to the desired effect. Preferable examples of an emulsifier include polyoxyethylene alkylaryl ether and polyoxyethylene sorbitan monolaurate. Preferable examples of a dispersing agent include lignin sulfonate, and dibutylnaphthalene sulfonate. Preferable examples of a wetting agent include alkyl sulfonates and alkylphenyl sulfonates.

Some formulations are used in undiluted form, whereas other formulations are used in diluted form which is diluted to a predetermined concentration with a diluent such as water. In a case where a formulation is diluted to obtain a spray solution for use, it is preferable that the spray solution contains Compound (I(-)) or Compound (I(+)) in an amount of 0.001% to 1.0%.

(4) Method of Controlling Plant Diseases

A plant disease controlling agent containing Compound (I(-)) or Compound (I(+)) can be used not only for foliage treatment (spray to stems and leaves), but also for non-foliage treatment such as seed treatment, soil drenching treatment and water surface treatment. The non-foliage treatment requires less work than the foliage treatment.

The seed treatment with the plant disease controlling agent is carried out in the following manner: seeds are mixed with the plant disease controlling agent in the form of wettable powder or dust etc. and stirred, or seeds are immersed in diluted wettable powder etc., whereby the plant disease controlling agent is caused to adhere to the seeds. The amount of Compound (I(-)) or Compound (I(+)) used for the seed treatment is 0.01 g to 10000 g, and preferably 0.1 g to 1000 g, with respect to 100 kg of the seeds.

The soil drenching treatment with the plant disease controlling agent is carried out, for example, in the following manner: the plant disease controlling agent in the form of granules etc. is placed in or around planting holes when, for example, seedlings are transplanted or (i) the plant disease controlling agent in the form of granules or wettable powder etc. are placed in or on soil around seeds or plants. The amount of Compound (I(-)) or Compound (I(+)) used for the soil drenching treatment is 0.01 g to 10000 g, and preferably 0.1 g to 1000 g, with respect to 1 $m^2$ of agro-horticultural field.

The water surface treatment with the plant disease controlling agent is carried out in the following manner: the plant disease controlling agent in the form of granules etc. is applied to water in a paddy field. The amount of Compound (I(-)) or Compound (I(+)) used for the water surface treatment is 0.1 g to 10000 g, and preferably 1 g to 1000 g, with respect to 10 a. of paddy field.

Since the concentration and amount of the plant disease controlling agent may vary depending on the dosage form, timing of use, method of use, place of use, target plant and the like, they are not limited to the foregoing ranges and can be increased or reduced.

The amount of Compound (I(-)) or Compound (I(+)) used for foliage spray treatment is 20 g to 5000 g, and more preferably 50 g to 2000 g, with respect to 1 ha of agro-horticultural field such as field, paddy field, orchard or greenhouse.

Furthermore, Compound (I(-)) or Compound (I(+)) can each be used in combination with other active ingredient(s). Examples of other active ingredients include bactericides, insecticides, acaricides, and herbicides, such as those listed below. A plant disease controlling agent containing Compound (I(-)) or Compound (I(+)) and such active ingredient(s) is more effective.

<Anti-Microorganism Substances>

Acibenzolar-S-methyl, 2-phenylphenol (OPP), azaconazole, azoxystrobin, amisulbrom, bixafen, benalaxyl, benomyl, benthiavalicarb-isopropyl, bicarbonate, biphenyl, bitertanol, blasticidin-S, borax, Bordeaux mixture, boscalid, bromuconazole, bronopol, bupirimate, sec-butylamine, calcium polysulphide, captafol, captan, carbendazim, carboxin, carpropamid, quinomethionate, chloroneb, chloropicrin, chlorothalonil, chlozolinate, cyazofamid, cyflufenamid, cymoxanil, cyproconazole, cyprodinil, dazomet, debacarb, dichlofluanid, diclocymet, diclomezine, dicloran, diethofencarb, difenoconazole, diflumetorim, dimethomorph, dimethoxystrobin, diniconazole, dinocap, diphenylamine, dithianon, dodemorph, dodine, edifenphos, epoxiconazole, ethaboxam, ethoxyquin, etridiazole, enestroburin, famoxadone, fenamidone, fenarimol, fenbuconazole, fenfuram, fenhexamid, fenoxanil, fenpiclonil, fenpropidin, fenpropimorph, fentin, ferbam, ferimzone, fluazinam, fludioxonil, flumorph, fluoroimide, fluoxastrobin, fluquinconazole, flusilazole, flusulfamide, flutolanil, flutriafol, folpet, fosetyl-A1, fuberidazole, furalaxyl, furametpyr, fluopicolide, fluopyram, guazatine, hexachlorobenzene, hexaconazole, hymexazol, imazalil, imibenconazole, iminoctadine, ipconazole, iprobenfos, iprodione, iprovalicarb, isoprothiolane, isopyrazam, isotianil, kasugamycin, copper preparations (such as copper hydroxide, copper naphthenate, copper oxychloride, copper sulphate, copper oxide, oxine-copper), kresoxim-methyl, mancopper, mancozeb, maneb, mandipropamid, mepanipyrim, mepronil, metalaxyl, metconazole, metiram, metominostrobin, mildiomycin, myclobutanil, nitrothal-isopropyl, nuarimol, ofurace, oxadixyl, oxolinic acid, oxpoconazole, oxycarboxin, oxytetracycline, pefurazoate, orysastrobin, penconazole, pencycuron, penthiopyrad, pyribencarb, fthalide, picoxystrobin, piperalin, polyoxin, probenazole, prochloraz, procymidone, propamocarb, propiconazole, propineb, proquinazid, prothioconazole, pyraclostrobin, pyrazophos, pyrifenox, pyrimethanil, pyroquilon, quinoxyfen, quintozene, silthiopham, simeconazole, spiroxamine, sulfur and sulfur preparations, tebuconazole, tecloftalam, tecnazen, tetraconazole, thiabendazole, thifluzamide, thiophanate-methyl, thiram, thiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, amisulbrom, sedaxane, flutianil, valiphenal, ametoctradin, dimoxystrobin, metrafenone, hydroxyisoxazole, metasulfocarb and the like.

<Insecticides/Acaricides/Nematocides>

Abamectin, acephate, acrinathrin, alanycarb, aldicarb, allethrin, amitraz, avermectin, azadirachtin, azamethiphos, azinphos-ethyl, azinphos-methyl, azocyclotin, *Bacillus firmus, Bacillus subtilis, Bacillus thuringiensis*, bendiocarb, benfuracarb, bensultap, benzoximate, bifenazate, bifenthrin, bioallethrin, bioresmethrin, bistrifluoron, buprofezin, butocarboxim, butoxycarboxim, cadusafos, carbaryl, carbofuran, carbosulfan, cartap, CGA50439, chlordane, chlorethoxyfos, chlorphenapyr, chlorfenvinphos, chlorfluazuron, chlormephos, chlorpyrifos, chlorpyrifos methyl, chromafenozide, clofentezine, clothianidin, chlorantraniliprole, coumaphos, cryolite, cyanophos, cycloprothrin, cyfluthrin, cyhalothrin, cyhexatin, cypermethrin, cyphenothrin, cyromazine, Cyazapyr, cyenopyrafen, DCIP, DDT, deltamethrin, demeton-5-methyl, diafenthiuron, diazinon, dichlorophen, dichloropropene, dichlorvos, dicofol, dicrotophos, dicyclanil, diflubenzuron, dimethoate, dimethylvinphos, dinobuton, dinotefuran, emamectin, endosulfan, EPN, esfenvalerate, ethiofencarb, ethion, ethiprole, ethofenprox, ethoprophos, etoxazole, famphur, fenamiphos, fenazaquin, fenbutatin oxide, fenitrothion, fenobucarb, fenothiocarb, fenoxycarb, fenpropathrin, fenpyroximate, fenthion, fenvalerate, fipronil, flonicamid, fluacrypyrim, flucycloxuron, flucythrinate, flufenoxuron, flumethrin, fluvalinate, flubendiamide, formetanate, fosthiazate, halfenprox, furathiocarb, halofenozide, gamma-HCH, heptenophos, hexaflumuron, hexythiazox, hydramethylnon, imidacloprid, imiprothrin, indoxacarb, isoprocarb, isoxathion, lufenuron, malathion, mecarbam, metam, methamidophos, methidathion, methiocarb, methomyl, methoprene, methothrin, methoxyfenozide, metolcarb, milbemectin, monocrotophos, naled, nicotine, nitenpyram, novaluron, noviflumuron, omethoate, oxamyl, oxydemethon methyl, parathion, permethrin, phenthoate, phorate, phosalone, phosmet, phosphamidon, phoxim, pirimicarb, pirimiphos-methyl, profenofos, propoxur, prothiophos, pymetrozin, pyrachlophos, pyrethrin, pyridaben, pyridalyl, pyrimidifen, pyriproxifen, pyrifluquinazon, pyriprole, quinalphos, silafluofen, spinosad, spirodiclofen, spiromesifen, spirotetramat, sulfluramid, sulphotep, SZI-121, tebufenozid, tebufenpyrad, tebupirimphos, teflubenzuron, tefluthrin, temephos, terbufos, tetrachlorvinphos, thiacloprid, thiamethoxam, thiodicarb, thiofanox, thiometon, tolfenpyrad, tralomethrin, tralopyril, triazamate, triazophos, trichlorfon, triflumuron, vamidothion, valifenal, XMC, xylylcarb, imicyafos, lepimectin and the like.

<Plant Growth Regulators>

Ancymidol, 6-benzylaminopurine, paclobutrazol, diclobutrazole, uniconazole, methylcyclopropene, mepiquat chloride, ethefon, chlormequat chloride, inabenfide, prohexadione and its salts, trinexapac-ethyl and the like. As plant hormones, jasmonic acid, brassinosteroid, gibberellin and the like.

It should be noted that a seed treated with the foregoing plant disease controlling agent is also encompassed in the scope of the present invention. Since the treatment with the plant disease controlling agent has been described earlier, its description is omitted here. A seed treated with the plant disease controlling agent can be used in the same manner as a seed that has not been treated with the plant disease controlling agent.

Also note that the plant disease controlling agent containing Compound (I(−)), which by definition contains Compound (I(−)), may also contain an enantiomer of Compound (I(−)), that is, it may also contain Compound (I(+)) which is (+)-enantiomer. However, for higher effect of Compound (I(−)) as an active ingredient, the amount of Compound (I(+)), which is the (+)-enantiomer, is preferably smaller than the amount of Compound (I(−)) ((−)-enantiomer), more preferably equal to or less than 40% of the amount of Compound (I(−)), and further preferably equal to or less than 20% of the amount of Compound (I(−)). It is particularly preferable that no Compound (I(+)) (i.e., (+)-enantiomer) is contained.

Likewise, the plant disease controlling agent containing Compound (I(+)), which by definition contains Compound (I(+)), may also contain an enantiomer of Compound (I(+)), that is, it may also contain Compound (I(−)) which is (−)-enantiomer. However, for higher effect of Compound (I(+)) as an active ingredient, the amount of Compound (I(−)), which is the (−)-enantiomer, is preferably smaller than the amount of Compound (I(+)) ((+)-enantiomer), more preferably equal to or less than 40% of the amount of Compound (I(+)), and further preferably equal to or less than 20% of the amount of Compound (I(+)). It is particularly preferable that no Compound (I(−)) (i.e., (−)-enantiomer) is contained.

The following description provides Examples to further specifically explain the embodiments of the present invention. It is needless to say that the present invention is not limited these Examples, and details thereof can take various aspects. The present invention is not limited to the description of the embodiment above, but may be altered within the scope of the claims. An embodiment based on a proper combination of technical means disclosed in different embodiments is encompassed in the technical scope of the present invention.

Further, all the literatures cited in this specification are of assistance as references in this specification.

EXAMPLES

Production Example 1

Synthesis of 1-(4-chlorobenzyl)-3-methyl-3-hydroxymethyl-2-oxocyclopentanecarboxylic acid methyl ester (Compound (8))

[Chem. 10]

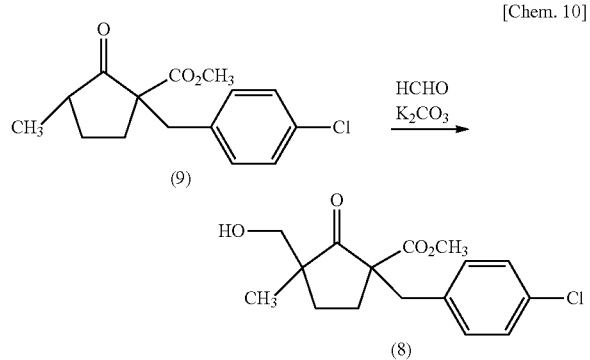

37% formaldehyde aqueous solution (12 mmol) and potassium carbonate (2.0 mmol) were added to 1-(4-chlorobenzyl)-3-methyl-2-oxocyclopentanecarboxylic acid methyl ester (Compound (9)) (4.0 mmol), and the resulting mixture was vigorously stirred at room temperature for 4 hours to cause a reaction. After the reaction, water was added to the resulting mixture, and extraction with ethyl acetate was performed. An organic layer of the extract was washed with saturated brine, and dried with anhydrous sodium sulfate. The solvent was distilled off, followed by purification of the residue by silica gel column chromatography, and thus Compound (8) was obtained as a mixture of two isomers.

Isomer (a):
  Yield: 18%
Isomer (b):
  Yield: 76%

Production Example 2

Synthesis of 5-(4-chlorobenzyl)-2-methoxymethoxymethyl-2-methylcyclopentanone (Compound (6))

[Chem. 11]

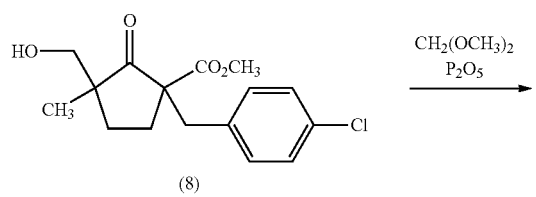

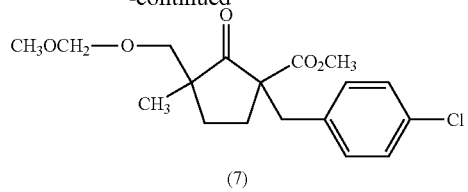

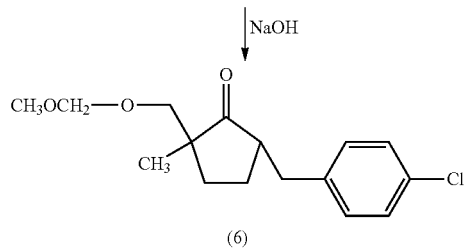

Compound (8) (0.60 mmol) was dissolved in methylene chloride (5.6 ml), and then dimethoxymethane (2.8 ml) was added to the solution. The resulting solution was cooled down, and diphosphorus pentoxide (372 mg) was then added to the solution. Then, the solution was vigorously stirred at room temperature for 10 minutes to cause a reaction. After the reaction, the reaction solution was added to saturated brine, and then extraction with diethyl ether was performed. An organic layer of the extract was washed with saturated brine, and then dried with the use of anhydrous sodium sulfate. The solvent was distilled off from the resultant and then the resultant was dried under reduced pressure. Thus crude 1-(4-chlorobenzyl)-3-methoxymethoxymethyl-3-methyl-2-oxocyclopentanecarboxylic acid methyl ester (Compound (7)) was obtained.

Compound (7) thus obtained was dissolved in isopropanol (0.53 ml). 2M aqueous sodium hydroxide (1.12 mmol) was added to the solution, and the resulting solution was stirred at a temperature of 60° C. for 1 hour to cause a reaction. After the reaction, water was added, and then extraction with ethyl acetate was performed. An organic layer of the extract was washed with saturated brine, and then dried with the use of anhydrous sodium sulfate. The solvent was distilled off, followed by purification of the residue by silica gel column chromatography, and thus Compound (6) was obtained as a mixture of two isomers.

Yield: 66%

Production Example 3

Synthesis of 5-(4-chlorobenzyl)-2-methoxymethoxymethyl-2-methyl-1-(1H-1,2,4-triazole-1-ylmethyl)cyclopentanol (Compound (4))

[Chem. 12]

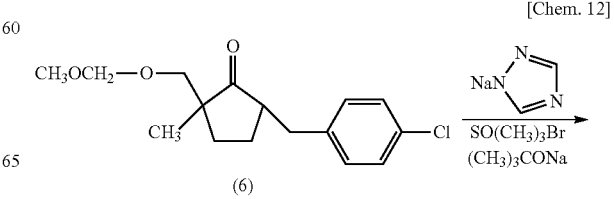

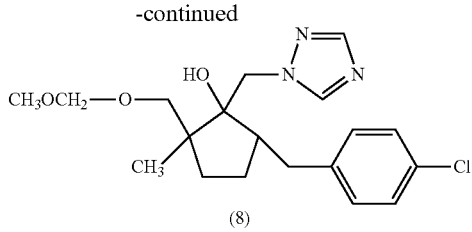

1H-1,2,4-triazolesodium salt (13.1 mmol) was dissolved in NMP (7 ml), and then heated to an internal temperature of 115° C. To this, Compound (6) (8.76 mmol) was added, and the mixture was thoroughly washed with NMP (1.8 ml). After the internal temperature was returned to 115° C., sodium t-butoxide (5.26 mmol) and trimethyl sulfoxonium bromide (1.476 mmol) were gradually added to the mixture over a period of 3 hours. After the addition, the resulting mixture was stirred at a temperature of 115° C. for 75 minutes. After the reaction solution was cooled down to 35° C., water was added to the reaction solution, and then extraction with ethyl acetate was performed. An organic layer of the extract was washed with water and saturated brine, and then dried with anhydrous sodium sulfate. The solvent was distilled off, followed by purification of the residue by silica gel column chromatography, and thus Compound (4), which was a mixture of isomers, was obtained.

Yield: 71%

Production Example 4

Synthesis of 5-(4-chlorobenzyl)-2-hydroxymethyl-2-methyl-1-(1H-1,2,4-triazole-1-ylmethyl)cyclopentanol (Compound (3))

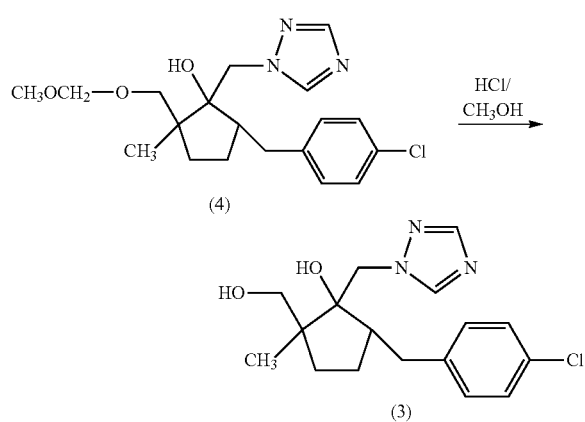

[Chem. 13]

Compound (4) (1.66 mmol) was dissolved in methanol (6.3 ml). To this, 10% hydrogen chloride-methanol (1.73 mmol) was added, and the mixture was stirred at room temperature for 48 hours. After the reaction, the solvent was distilled off, and then water was added to the resulting mixture. Ethyl acetate was further added, and then aqueous sodium hydroxide was further added until pH 10 was attained. Then, an organic layer of the mixture was separated from the rest of the mixture, washed with saturated brine, and then dried with anhydrous sodium sulfate. The solvent was distilled off, thereby obtaining Compound (3) in the form of a plurality of isomers (Compound (3-1)(1,2-cis, 1,5-cis):Compound (3-2)(1,2-trans, 1,5-cis):other geometrical isomers=6:3:1).

Production Example 5

Synthesis of (1,2-cis, 1,5-cis)-5-(4-chlorobenzyl)-2-methyl-2-[(4-methylphenyl) sulfonyloxymethyl]-1-(1H-1,2,4-triazole-1-ylmethyl)cyclopentanol (Compound (2))

[Chem. 14]

In argon atmosphere, sodium hydride (1.83 mmol) was washed with hexane, suspended in dehydrated THF (4 ml), and then cooled down. To this suspension, then, Compound (3-1) (1.52 mmol) dissolved in dehydrated THF (5 ml) was added by dropping. The temperature of the mixture was returned to room temperature, and then stirred for 30 minutes. Then, the mixture was again cooled down. Then, p-toluenesulfonyl chloride (1.97 mmol) was added to the mixture, and the resulting mixture was stirred for 1.5 hours while being kept cool. Then, the mixture was further stirred at room temperature for another 0.5 hour. Then water was added to the reaction solution to stop the reaction, and then the resulting solution was partitioned with the use of ethyl acetate. After that, an organic layer was washed with saturated brine, dried with anhydrous sodium sulfate, and then concentrated. Then purification was performed by silica gel column chromatography, and thus Compound (2) was obtained.

Yield: 55%

Production Example 6

Synthesis of (1,2-cis, 1,5-cis)-5-(4-chlorobenzyl)-2-chloromethyl-2-methyl-1-(1H-1,2,4-triazole-1-ylmethyl)cyclopentanol (Compound (1'))

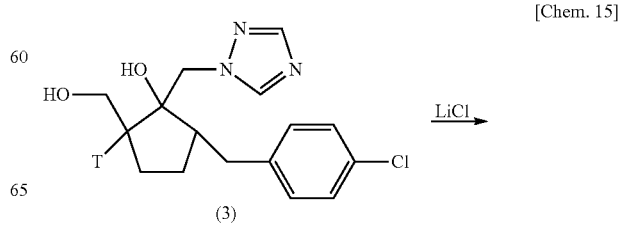

[Chem. 15]

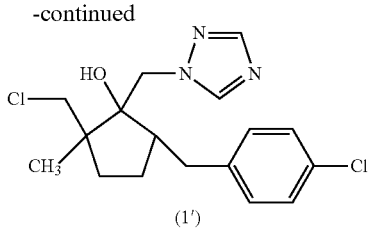

(1')

In argon atmosphere, Compound (2) (0.0245 mmol) was dissolved in dehydrated DMF (0.24 ml). To this solution, lithium chloride (0.245 mmol) was added, and the resulting solution was stirred at a temperature of 100° C. for 1.5 hours. Then, ethyl acetate was added to the reaction solution, and the resulting solution was washed with saturated brine. Then, an organic layer was dried with anhydrous sodium sulfate, and then concentrated. Then, purification was performed by silica gel column chromatography so as to obtain Compound (1') which was a racemic compound.

Yield: 58%

Production Example 7

Preparation of (−)-enantiomer and (+)-enantiomer of (1,2-cis, 1,5-cis)-5-(4-chlorobenzyl)-2-chloromethyl-2-methyl-1-(1H-1,2,4-triazole-1-ylmethyl)cyclopentanol Compound (1') in the form of a racemic compound was dissolved in ethanol, and then underwent preparative separation by being subjected to high performance liquid chromatography (HPLC) with a semi-preparative column in which amylose tris(3,5-dimethylphenylcarbamate) was fixed to a silica gel support.

The specific conditions were as follows:
High-performance liquid chromatograph: LC-9A (manufactured by Shimazu Corporation)
Semi-preparative column: product name "CHIRALPAK IA", manufactured by Dicel Chemical Industries, Ltd., inner diameter −20 mm, length −250 mm, particle size −5 μm
Sample concentration: 50,000 ppm (in ethanol)
Mobile phase: hexane:ethanol (20:1)
Flow rate: 3.5 ml/min
Detection wavelength: 254 nm The separation was performed under the above conditions, and, as a result, two different peaks were observed at different elution times. Measurement of specific rotations of the respective compounds of the two different peaks showed that (i) the compound eluted first was a dextrorotatory enantiomer ((+)-enantiomer) and (ii) the compound eluted later was a levorotatory enantiomer ((−)-enantiomer). Hereinafter, the (+)-enantiomer is referred to as Compound (1-1b) and the (−)-enantiomer is referred to as Compound (1-1a).

With the use of P-1020 (manufactured by JASCO Corporation, Na Lamp: 589 nm), (i) the measurement of the specific rotation of Compound (1-1b) was carried out 5 times and (ii) the measurement of the specific rotation of Compound (1-1a) was carried out 14 times. The specific measurements are as follows:

Average specific rotation of Compound (1-1b): $[\alpha]_D^{22}$ +21.9° (20 mg for each 2 ml of chloroform)
Average specific rotation of Compound (1-1a): $[\alpha]_D^{22}$ = −21.2° (20 mg for each 2 ml of chloroform)

Production Example 8

Production of (−)-enantiomer and (+)-enantiomer of 5-(4-fluorobenzyl)-2-chloromethyl-2-methyl-1-(1H-1,2,4-triazole-1-ylmethyl)cyclopentanol (−)-Enantiomer and (+)-enantiomer of (1,2-cis, 1,5-cis)-5-(4-fluorobenzyl)-2-chloromethyl-2-methyl-1-(1H-1,2,4-triazole-1-ylmethyl)cyclopentanol were produced according to the method of Production Examples 1 through 7 with the use of, as starting material, 1-(4-fluorobenzyl)-3-methyl-2-oxocyclopentanecarboxylic acid methyl ester instead of 1-(4-chlorobenzyl)-3-methyl-2-oxocyclopentanecarboxylic acid methyl ester. Hereinafter, the (−)-enantiomer is referred to as Compound (1-2a), and the (+)-enantiomer is referred to as Compound (1-2b).

Production Example 9

Preparation of (−)-enantiomer and (+)-enantiomer of 5-benzyl-2-chloromethyl-2-methyl-1-(1H-1,2,4-triazole-1-ylmethyl)cyclopentanol (−)-Enantiomer and (+)-enantiomer of (1,2-cis, 1,5-cis)-5-benzyl-2-chloromethyl-2-methyl-1-(1H-1,2,4-triazole-1-ylmethyl)cyclopentanol were produced according to the method of Production Examples 1 through 7 with the use of, as starting material, 1-benzyl-3-methyl-2-oxocyclopentanecarboxylic acid methyl ester instead of 1-(4-chlorobenzyl)-3-methyl-2-oxocyclopentanecarboxylic acid methyl ester.

Formulation Example 1

Wettable Powder

| Compound (1-1a) | 50 parts |
| --- | --- |
| Lignin sulfonate | 5 parts |
| Alkyl sulfonate | 3 parts |
| Diatomaceous earth | 42 parts |

These were ground and blended to form wettable powder, and the wettable powder was diluted with water for use.

Formulation Example 2

Dust

| Compound (1-1a) | 3 parts |
| --- | --- |
| Clay | 40 parts |
| Talc | 57 parts |

These were ground and blended to obtain dusting powder for use.

Formulation Example 3

Granules

| | |
|---|---|
| Compound (1-1a) | 5 parts |
| Bentonite | 43 parts |
| Clay | 45 parts |
| Lignin sulfonate | 7 parts |

These were mixed uniformly, water was added to the resulting mixture, and the mixture was kneaded. The mixture was processed into granules and dried by an extruding granulator. In this way, granules were obtained.

Formulation Example 4

Emulsifiable Concentrate

| | |
|---|---|
| Compound (1-1a) | 20 parts |
| Polyoxyethylene alkylaryl ether | 10 parts |
| Polyoxyethylene sorbitan monolaurate | 3 parts |
| Xylene | 67 parts |

These were mixed and dissolved uniformly to obtain an emulsifiable concentrate.

Formulation Example 5

Wettable Powder

| | |
|---|---|
| Compound (1-1b) | 50 parts |
| Lignin sulfonate salt | 5 parts |
| Alkyl sulfonate salt | 3 parts |
| Diatomaceous earth | 42 parts |

These were ground and blended to form wettable powder, and the wettable powder was diluted with water for use.

Formulation Example 6

Dust

| | |
|---|---|
| Compound (1-1b) | 3 parts |
| Clay | 40 parts |
| Talc | 57 parts |

These were ground and blended to obtain dusting powder for use.

Formulation Example 7

Granules

| | |
|---|---|
| Compound (1-1b) | 5 parts |
| Bentonite | 43 parts |
| Clay | 45 parts |
| Lignin sulfonate salt | 7 parts |

These were mixed uniformly, water was added to the resulting mixture, and the mixture was kneaded. The mixture was processed into granules and dried by an extruding granulator. In this way, granules were obtained.

Formulation Example 8

Emulsifiable Concentrate

| | |
|---|---|
| Compound (1-1b) | 20 parts |
| Polyoxyethylene alkylaryl ether | 10 parts |
| Polyoxyethylene sorbitan monolaurate | 3 parts |
| Xylene | 67 parts |

These were mixed and dissolved uniformly to obtain an emulsifiable concentrate.

Experiment Example 1

Test 1 for Examining Controlling Effect on Cucumber Gray Mold by Foliage Spray Treatment Compound (1-1a) and Compound (1-2a) in the form of wettable powder (such as that described in Formulation Example 1) were each suspended in water so that the suspension had a certain concentration (3.1 mg/L or 12.5 mg/L), and the suspension was sprayed at a rate of 1,000 L/ha to leaves of cucumber plants (cultivar: SHARP1) in their cotyledon stage. The cucumber plants had been grown in square plastic pots (6 cm×6 cm). After the suspension was then left to dry, paper discs (8 mm in diameter) impregnated with a spore suspension of *Botrytis cinerea* were placed on the leaves, and the plants were kept at 20° C. in a high humidity environment. Four days after inoculation, the lesion degree of the cucumber gray mold was examined in accordance with the criteria shown in Table 1, and the protective values were calculated by the following equation:

Protective value (%)=(1−Average lesion degree in sprayed plot/Average lesion degree in unsprayed plot)×100.

TABLE 1

| Lesion Degree | Percentage of affected area |
|---|---|
| 0 | Not affected |
| 0.5 | Percentage of area of lesions is less than 5% |
| 1 | Percentage of area of lesions is not less than 5% but less than 10% |
| 2 | Percentage of area of lesions is not less than 10% but less than 25% |
| 3 | Percentage of area of lesions is not less than 25% but less than 50% |
| 4 | Percentage of area of lesions is not less than 50% but less than 80% |
| 5 | Percentage of area of lesions is 80% or greater |

The results are shown in Table 2 and 3. It should be noted that, in the present experiment example and the subsequent experiment examples, controls used in the disease control tests are formulations obtained from Compound (1-1b) and Compound (1-2b) instead of Compound (1-1a) and Compound (1-2a), respectively.

TABLE 2

| Compound | Cucumber gray mold | |
|---|---|---|
| | Compound (1-1a) | Compound (1-1b) |
| Concentration | 12.5 mg/L | 12.5 mg/L |
| Protective value (%) | 100 | 45 |

TABLE 3

| | Cucumber gray mold | | | |
|---|---|---|---|---|
| Compound | Compound (1-2a) | | Compound (1-2b) | |
| Concentration | 12.5 mg/L | 3.1 mg/L | 12.5 mg/L | 3.1 mg/L |
| Protective value (%) | 100 | 40 | 98 | 15 |

Experiment Example 2

Test 1 for Examining Controlling Effect on Wheat Brown Rust by Foliage Spray Treatment Compound (1-1a) and Compound (1-2a) in the form of wettable powder (such as that described in Formulation Example 1) were each suspended in water so that the suspension had a certain concentration (0.8 mg/L), and the suspension was sprayed at a rate of 1,000 L/ha to leaves of wheat plants (cultivar: NORIN No. 61) in their second leaf stage. The wheat plants had been grown in square plastic pots (6 cm×6 cm). The suspensions were left to dry, and inoculated with spores of *Puccinia recondita* (adjusted at 200 spores per field of vision, Gramin S was added at 60 ppm) by spraying, and kept at 25° C. in a high humidity environment for 48 hours. After that, the plants were kept in a greenhouse. 11 days after the inoculation, the lesion degree of the wheat leaf rust was examined in accordance with the criteria shown in Table 4, and the protective values were calculated by the following equation.

Protective value (%)=(1−Average lesion degree in sprayed plot/Average lesion degree in unsprayed plot)×100

TABLE 4

| Lesion Degree | Percentage of affected area |
|---|---|
| 0 | Not affected |
| 0.5 | Percentage of affected area is less than 1% |
| 1 | Percentage of affected area is not less than 1% but less than 5% |
| 2 | Percentage of affected area is not less than 5% but less than 10% |
| 3 | Percentage of affected area is not less than 10% but less than 30% |
| 4 | Percentage of affected area is not less than 30% but less than 50% |
| 5 | Percentage of affected area is 50% or greater |

The results are shown in Tables 5 and 6.

TABLE 5

| | Wheat leaf rust | |
|---|---|---|
| Compound | Compound (1-1a) | Compound (1-1b) |
| Protective value (%) | 95 | 29 |

TABLE 6

| | Wheat leaf rust | |
|---|---|---|
| Compound | Compound (1-2a) | Compound (1-2b) |
| Protective value (%) | 91 | 80 |

Experiment Example 3

Test 1 for Examining Controlling Effect on Wheat Powdery Mildew by Foliage Spray Treatment Compound (1-1a) in the form of wettable powder (such as that described in Formulation Example 1) was suspended in water so that the suspension had a certain concentration (12.5 mg/L). The suspension was sprayed at 1,000 L/ha to leaves of wheat plants (cultivar: NORIN No. 61) in their second leaf stage. The wheat plants had been grown in square plastic pots (6 cm×6 cm). After the suspension was left to dry, the plants were inoculated with *Erysiphe graminis* f. sp *tritici* taken from wheat plants infected with wheat powdery mildew, by sprinkling. 8 days and 11 days after the inoculation, the lesion degree of the wheat powdery mildew was examined in accordance with the criteria shown in Table 4. The protective values were found in the same way as in Experiment Example 2. The results are shown in Table 7.

TABLE 7

| | Wheat powdery mildew | |
|---|---|---|
| Compound | Compound (1-1a) | Compound (1-1b) |
| Protective value (%) (8 days after treatment) | 96 | 71 |
| Protective value (%) (11 days after treatment) | 84 | 58 |

Experiment Example 4

Efficacy of Seed Treatment on Wheat Brown Rust

A pot experiment was performed to evaluate the efficacy of seed treatment in controlling wheat leaf rust. Compound (1-1a) and Compound (1-2a), each of which was dissolved in DMSO to make up such a concentration that the seeds would be treated in treatment amount of 20 g ai/100 kg seeds, were each applied to wheat seeds in a vial, and thereafter 8 wheat seeds were sowed on an 80-cm² pot. The pot was kept in a greenhouse with water supplied to its bottom. 21 days after the sowing, the wheat seeds were inoculated with *Puccinia recondita*, and kept in a wet box for 2 days. After that, the pot was again kept in the greenhouse with water supplied to its bottom. 12 days after the inoculation, the percentage of affected area was found, and the protective value was calculated by the following equation.

Protective value (%)=(1−(Percentage of affected area in treated region/Percentage of affected area in untreated region))×100

The results are shown in Tables 8 and 9. As described later, the growth of the seeds, which were treated with a plant disease controlling agent containing Compound (1-2b), was inhibited, and it was therefore not possible to measure protective values.

TABLE 8

| Compound | Compound (1-1a) | Compound (1-1b) |
|---|---|---|
| Protective value (%) | 90 | 63 |

TABLE 9

| Compound | Compound (1-2a) | Compound (1-2b) |
|---|---|---|
| Protective value (%) | 100 | — |

Experiment Example 5

Growth Inhibition (Adverse Effects) of Seed Treatment on Wheat Seeds

A pot experiment was performed to evaluate the growth inhibition (adverse effects) caused by the seed treatment. Compound (1-1a) and Compound (1-2a), each of which was dissolved in DMSO to make up such a concentration that the seeds would be treated in treatment amount of 2 g to 200 g ai/100 kg seeds, were each applied to wheat seeds in a vial, and thereafter 8 wheat seeds were sowed in an 80-cm$^2$ pot. The pot was kept in a greenhouse with water supplied to its bottom. 20 days after the sowing, a growth measure of wheat was evaluated. A growth inhibition index was calculated based on the criteria shown by Table 10. In Table 10, a smaller growth inhibition index indicates a lesser adverse effect of growth inhibition caused by the treatment with the use of a plant disease controlling agent.

TABLE 10

| Growth measure (in untreated division) | Growth inhibition index |
|---|---|
| 50% or more | 0 |
| Less than 50% but 40% or more | 1 |
| Less than 40% but 30% or more | 2 |
| Less than 30% but 20% or more | 3 |
| Less than 20% but 10% or more | 4 |
| Less than 10% | 5 |

The results are shown in Tables 11 and 12.

TABLE 11

| Compound | Compound (1-1a) | | | Compound (1-1b) | | |
|---|---|---|---|---|---|---|
| Treatment amount (g ai/100 kg seeds) | 200 | 20 | 2 | 200 | 20 | 2 |
| Growth inhibition index | 0 | 0 | 0 | 4 | 4 | 0 |

TABLE 12

| Compound | Compound (1-2a) | | | Compound (1-2b) | | |
|---|---|---|---|---|---|---|
| Treatment amount (g ai/100 kg seeds) | 200 | 20 | 2 | 200 | 20 | 2 |
| Growth inhibition index | 2 | 0 | 0 | 5 | 4 | 0 |

Experiment Example 6

Necrosis (Adverse Effects) of Seed Treatment on Wheat Seeds

A pot experiment was performed to evaluate necrosis (adverse effects) caused by the seed treatment. Compound (1-1a) and Compound (1-2a), each of which was dissolved in DMSO to make up such a concentration that the seeds would be treated in treatment amount of 2 g to 200 g ai/100 kg seeds, were each applied to wheat seeds in a vial, and thereafter 8 wheat seeds were sowed in an 80-cm$^2$ pot. The pot was kept in a greenhouse with water supplied to its bottom. 20 days after the sowing, an extent of necrosis (percentage of necrotic surface area) of wheat was evaluated. A necrosis index was derived from the percentage of the necrotic surface area, based on the criteria shown by Table 13. In Table 13, a smaller necrosis index indicates a lesser adverse effect of necrosis caused by the treatment with the use of a plant disease controlling agent.

TABLE 13

| Percentage of necrotic surface area | Necrosis index |
|---|---|
| Less than 1% | 0 |
| Less than 5% but not less than 1% | 1 |
| Less than 20% but not less than 5% | 2 |
| 20% or more | 3 |

The results are shown in Tables 14 and 15.

TABLE 14

| Compound | Compound (1-1a) | | | Compound (1-1b) | | |
|---|---|---|---|---|---|---|
| Treatment amount (g ai/100 kg seeds) | 200 | 20 | 2 | 200 | 20 | 2 |
| Necrosis index | 0 | 0 | 0 | 2 | 2 | 0 |

TABLE 15

| Compound | Compound (1-2a) | | | Compound (1-2b) | | |
|---|---|---|---|---|---|---|
| Treatment amount (g ai/100 kg seeds) | 200 | 20 | 2 | 200 | 20 | 2 |
| Necrosis index | 0 | 0 | 0 | 3 | 3 | 0 |

Experiment Example 7

Efficacy of Seed Treatment on Rice Bakanae Disease

A pot experiment was performed to evaluate the effectiveness of the seed treatment in controlling rice Bakanae disease. Compound (1-1a), which was dissolved in DMSO to make up such a concentration that the seeds would be treated in treatment amount of 80 g ai/100 kg seeds, was applied in a vial to seeds of a rice plant infected with rice Bakanae disease, and thereafter 16 rice plant seeds were sowed in a 50-cm$^2$ pot. The pot was kept in a greenhouse with water supplied to its bottom. 20 days after the sowing, examination was conducted on the percentage of seedlings infected with rice leaf blight. Then, protective values were calculated as were in Experiment Example 4.

The results are shown in Table 16.

TABLE 16

| Compound | Compound (1-1a) | Compound (1-1b) |
|---|---|---|
| Treatment amount (g ai/100 kg seeds) | 80 | 80 |
| Protective value (%) | 100 | 66 |

Experiment Example 8

Growth Inhibition (Adverse Effects) of Seed Treatment on Rice Plant Seeds

A pot experiment was performed to evaluate the growth inhibition (adverse effects) caused by the seed treatment. Compound (1-1a), which was dissolved in DMSO to make up such a concentration that the seeds would be treated in treatment amount of 80 g ai/100 kg seeds, was applied to rice plant seeds in a vial, and thereafter 16 rice plant seeds were sowed in a 50-cm² pot. The pot was kept in a greenhouse with water supplied to its bottom. 20 days after the sowing, a growth measure of rice plant was evaluated. A growth inhibition index was calculated as was in Experiment Example 5.

The results are shown in Table 17.

TABLE 17

| Compound | Compound (1-1a) | Compound (1-1b) |
|---|---|---|
| Treatment amount (g ai/100 kg seeds) | 80 | 80 |
| Growth inhibition index | 0 | 4 |

Experiment Example 9

Necrosis (Adverse Effects) of Seed Treatment on Rice Plant Seeds

A pot experiment was performed to evaluate necrosis (adverse effects) caused by the seed treatment. Compound (1-1a), which was dissolved in DMSO to make up such a concentration that the seeds would be treated in treatment amount of 80 g ai/100 kg seeds, was applied to rice plant seeds in a vial, and thereafter 16 rice plant seeds were sowed in a 50-cm² pot. The pot was kept in a greenhouse with water supplied to its bottom. 20 days after the sowing, an extent of necrosis (percentage of necrotic surface area) of rice plant was evaluated. A necrosis index was calculated as was in Experiment Example 6.

The results are shown in Table 18.

TABLE 18

| Compound | Compound (1-1a) | Compound (1-1b) |
|---|---|---|
| Treatment amount (g ai/100 kg seeds) | 80 | 80 |
| Necrosis index | 0 | 2 |

Experiment Example 10

Test 1 for Antifungal Effect on Pathogenic Microorganisms

In Experiment Example 10, the antifungal effect on various plant fungal pathogens was tested.

Compound (1-1a) or Compound (1-2a) was dissolved in dimethyl sulfoxide, and the resulting solution was added to a PDA medium (potato dextrose-agar medium) at about 60° C. The medium and the solution were mixed thoroughly in a conical flask, poured into a petri dish, and allowed to solidify. In this way, a plate medium containing Compound (1-1a) or Compound (1-2a) at a certain concentration was prepared.

Meanwhile, test microorganisms cultured on a plate medium in advance were cut out with the use of a cork borer 4 mm in diameter, and were inoculated onto the compound-containing plate medium. After the inoculation, the microorganisms were cultured at their optimum growth temperatures (for example, refer to LIST OF CULTURES 1996 microorganisms 10th edition, Institute for Fermentation (foundation)) for 1 day to 7 days, and their growth was determined by measuring the diameter of their flora. The extent of growth of the microorganisms on the compound-containing plate medium was compared with that of microorganisms on a plate medium where no compound was added, and mycelial growth inhibition rate was calculated by the following equation:

$$R = 100(dc-dt)/dc$$

where R is mycelial growth inhibition rate (%), dc is the flora diameter in untreated plate, and dt is the flora diameter in plate treated with the compound.

The results were rated on a 1-to-5 scale in accordance with the criteria shown in Table 19. A larger antifungal index indicates a better antifungal effect.

TABLE 19

| Mycelial growth inhibition rate | Antifungal index |
|---|---|
| 90% or greater | 5 |
| Less than 90% but not less than 80% | 4 |
| Less than 80% but not less than 70% | 3 |
| Less than 70% but not less than 60% | 2 |
| Less than 60% | 1 |

The results are shown in Tables 20 and 21.

TABLE 20

| | | Compound (1-1a) | | | | | Compound (1-1b) | | | | |
|---|---|---|---|---|---|---|---|---|---|---|---|
| | Micro-organism | 2.50 mg/L | 1.25 mg/L | 0.63 mg/L | 0.31 mg/L | 0.16 mg/L | 2.50 mg/L | 1.25 mg/L | 0.63 mg/L | 0.31 mg/L | 0.16 mg/L |
| Antifungal index | P.n | 5 | 5 | 5 | 3 | 2 | 5 | 3 | 2 | 2 | 2 |
| | P.h | 5 | 5 | 5 | 5 | 1 | 4 | 3 | 2 | 1 | 1 |
| | M.n | 5 | 4 | 3 | 3 | 1 | 3 | 2 | 1 | 1 | 1 |

TABLE 20-continued

| | | Compound (1-1a) | | | | | Compound (1-1b) | | | | |
|---|---|---|---|---|---|---|---|---|---|---|---|
| | Micro-organism | 2.50 mg/L | 1.25 mg/L | 0.63 mg/L | 0.31 mg/L | 0.16 mg/L | 2.50 mg/L | 1.25 mg/L | 0.63 mg/L | 0.31 mg/L | 0.16 mg/L |
| | G.g | 5 | 5 | 5 | 5 | 3 | 5 | 5 | 2 | 1 | 1 |
| | R.s | 3 | 2 | 2 | 2 | 2 | 2 | 2 | 2 | 1 | 1 |
| | G.f | 5 | 5 | 5 | 5 | 5 | 5 | 5 | 5 | 4 | 3 |
| | R.o | 5 | 5 | 5 | 4 | 3 | 4 | 1 | 1 | 1 | 1 |
| | A.m | 5 | 5 | 4 | 4 | 1 | 5 | 4 | 4 | 3 | 1 |
| | S.s | 5 | 5 | 5 | 5 | 5 | 5 | 5 | 5 | 5 | 3 |
| | B.c | 5 | 5 | 5 | 5 | 3 | 5 | 4 | 3 | 1 | 1 |
| | G.c | 5 | 5 | 5 | 5 | 5 | 5 | 5 | 5 | 4 | 2 |
| | C.b | 5 | 5 | 5 | 5 | 4 | 5 | 5 | 5 | 4 | 3 |

TABLE 21

| | | Compound (1-2a) | | | | | Compound (1-2b) | | | | |
|---|---|---|---|---|---|---|---|---|---|---|---|
| | Micro-organism | 2.50 mg/L | 1.25 mg/L | 0.63 mg/L | 0.31 mg/L | 0.16 mg/L | 2.50 mg/L | 1.25 mg/L | 0.63 mg/L | 0.31 mg/L | 0.16 mg/L |
| Antifungal index | P.n | 5 | 5 | 5 | 2 | 1 | 5 | 3 | 2 | 1 | 1 |
| | M.n | 5 | 3 | 2 | 1 | 1 | 2 | 1 | 1 | 1 | 1 |
| | G.g | 5 | 5 | 5 | 4 | 1 | 5 | 5 | 4 | 1 | 1 |
| | G.f | 5 | 5 | 5 | 5 | 4 | 5 | 5 | 5 | 4 | 3 |
| | R.o | 5 | 5 | 3 | 1 | 1 | 2 | 1 | 1 | 1 | 1 |
| | S.s | 5 | 5 | 5 | 5 | 5 | 5 | 5 | 5 | 5 | 3 |
| | B.c | 5 | 5 | 5 | 5 | 3 | 5 | 5 | 5 | 3 | 1 |
| | G.c | 5 | 5 | 5 | 5 | 5 | 5 | 5 | 5 | 4 | 3 |

It should be noted that, in Tables 20 and 21, the abbreviations for the types of pathogens represent the following pathogens:

P.n: Wheat glume blotch (*Phaeosphaeria nodorum*)
P.h: Pathogen causing wheat eye spot (*Pseudocercoporella herpotrichoides*)
M.n: Pathogen causing wheat pink snow mold (*Microdochium nivale*)
G.g: Pathogen causing wheat take-all disease (*Gaeumannomyces graminis*)
R.s: Pathogen causing rice sheath blight (*Rhizoctonia solani*)
G.f: Pathogen causing rice bakanae disease (*Gibberella fujikuroi*)
R.o: Rice damping-off (*Rhizopus oryzae*)
A.m: Apple *alternaria* blotch (*Alternaria alternata*)
S.s: *Sclerotinia* rot (sclerotium) (*Sclerotinia sclerotiorum*)
B.c: Pathogen causing gray mold (*Botrytis cinerea*)
G.c: Pathogen causing anthracnose (*Glomerella cingurata*)
C.b: Sugar beet *cercpspora* leaf spot (*Cercospora beticola*)

Experiment Example 11

Test 2 for Antifungal Effect on Pathogenic Microorganisms

The antifungal effect on various plant fungal pathogens was tested.

Compound (1-1b) or Compound (1-2b) was dissolved in dimethyl sulfoxide, and the resulting solution was added to a PDA medium (potato dextrose-agar medium) at about 60° C. The medium and the solution were mixed thoroughly in a conical flask, poured into a petri dish, and allowed to solidify. In this way, a plate medium containing Compound (1-1b) or Compound (1-2b) at a certain concentration was prepared.

Meanwhile, test microorganisms cultured on a plate medium in advance were cut out with the use of a cork borer 4 mm in diameter, and were inoculated onto the compound-containing plate medium. After the inoculation, the pathogens were cultured at their optimum growth temperatures (for example, refer to LIST OF CULTURES 1996 microorganisms 10th edition, Institute for Fermentation (foundation)) for 1 day to 7 days, and their growth was determined by measuring the diameter of their flora. The extent of growth of the pathogens on the compound-containing plate medium was compared with that of pathogens on a plate medium where no compound was added, and mycelial growth inhibition rate was calculated as in Experiment Example 10. Note that, in Experiment Example 11, controls used in the antifungal effect tests are Compound (1-1a) and Compound (1-2a) instead of Compound (1-1b) and Compound (1-2b), respectively.

The results were rated on a 1-to-5 scale as in Experiment Example 10.

The results are shown in Tables 22 and 23.

TABLE 22

| | Sample Concentration | Microorganism | | | | |
|---|---|---|---|---|---|---|
| | mg/L | P.g. | U.n. | F.c. | P.i. | S.t. |
| Compound (1-1b) | 1.25 | 5 | 5 | 5 | 5 | 5 |
| | 0.63 | 5 | 4 | 5 | 5 | 5 |
| | 0.31 | 5 | 3 | 5 | 5 | 3 |
| | 0.16 | 5 | 2 | 4 | 5 | 1 |
| | 0.08 | 4 | 1 | 3 | 4 | 1 |
| | 0.04 | 3 | 1 | 1 | 3 | 1 |
| Compound (1-1a) | 1.25 | 5 | 4 | 5 | 5 | 1 |
| | 0.63 | 5 | 3 | 5 | 5 | 1 |
| | 0.31 | 5 | 2 | 4 | 5 | 1 |
| | 0.16 | 4 | 1 | 4 | 4 | 1 |
| | 0.08 | 3 | 1 | 3 | 4 | 1 |
| | 0.04 | 2 | 1 | 1 | 1 | 1 |

TABLE 23

| | Sample Concentration mg/L | Microorganism | | | | |
|---|---|---|---|---|---|---|
| | | P.g. | U.n. | F.c. | P.i. | S.t. |
| Compound (1-2b) | 1.25 | 5 | 5 | 5 | 5 | 5 |
| | 0.63 | 5 | 4 | 5 | 5 | 5 |
| | 0.31 | 5 | 4 | 4 | 5 | 5 |
| | 0.16 | 5 | 2 | 3 | 5 | 5 |
| | 0.08 | 5 | 1 | 2 | 4 | 5 |
| | 0.04 | 4 | 1 | 1 | 1 | 2 |
| Compound (1-2a) | 1.25 | 5 | 2 | 5 | 5 | 3 |
| | 0.63 | 5 | 1 | 4 | 5 | 1 |
| | 0.31 | 5 | 1 | 3 | 4 | 1 |
| | 0.16 | 4 | 1 | 2 | 3 | 1 |
| | 0.08 | 2 | 1 | 1 | 1 | 1 |
| | 0.04 | 1 | 1 | 1 | 1 | 1 |

It should be noted that, in Tables 22 and 23, the abbreviations for the types of pathogens represent the following pathogens:
S.t: Pathogen causing wheat leaf blight (*Septoria tritici*)
P.g: Pathogen causing barley stripe (*Pyrenophora graminea*)
U.n: Pathogen causing barley loose smut (*Ustilago nuda*)
F.c: Cucumber *fusarium* wilt (*Fusarium oxysporum*)
P.i: Blue mold of citrus fruits (*Penicillium italicum*)

Experiment Example 12

Test 2 for Effectiveness of Foliage Spray Treatment in Controlling Cucumber Gray Mold Compound (1-1b) and Compound (1-2b) in the form of wettable powder (such as that described in Formulation Example 5) were each suspended in water so that the suspension had a certain concentration (50 mg/L), and the suspension was sprayed at a rate of 1,000 L/ha to leaves of cucumber plants (cultivar: SHARP1) in their cotyledon stage. The cucumber plants had been grown in square plastic pots (6 cm×6 cm). After the leaves were air-dried, paper discs (8 mm in diameter) impregnated with a spore suspension of cucumber graymold-causing microorganisms were placed on the leaves, and the plants were kept at 20° C. in a high humidity environment. 4 days after the inoculation, the lesion degree of the cucumber gray mold was examined, and the protective values were calculated as were in Experiment Example 1.

The results revealed that Compound (1-1b) and Compound (1-2b) each showed a protective value of 90% and more.

Experiment Example 13

Test 2 For Effectiveness of Foliage Spray Treatment in Controlling Wheat Leaf Rust Compound (1-1b) and Compound (1-2b) in the form of wettable powder (such as that described in Formulation Example 5) were each suspended in water so that the suspension had a certain concentration (3.1 mg/L), and the suspension was sprayed at a rate of 1,000 L/ha to leaves of wheat plants (cultivar: NORIN No. 61) in their second leaf stage. The wheat plants had been grown in square plastic pots (6 cm×6 cm). The leaves were air-dried, and inoculated with spores of *Puccinia recondita* (adjusted at 200 spores per field of vision, Gramin S was added at 60 ppm) by spraying, and kept at 25° C. in a high humidity environment for 48 hours. After that, the plants were kept in a greenhouse. 11 days after the inoculation, the lesion degree of the wheat leaf rust was examined, and the protective values were calculated as were in Experiment Example 2.

The results revealed that Compound (1-1b) and Compound (1-2b) each showed a protective value of 90% or more.

Experiment Example 14

Test 2 for Effectiveness of Foliage Spray Treatment in Controlling Wheat Powdery Mildew Compound (1-1b) and Compound (1-2b) in the form of wettable powder (such as that described in Formulation Example 5) were each suspended in water so that the suspension had a certain concentration (50 mg/L). The suspension was sprayed at 1,000 L/ha to leaves of wheat plants (cultivar: NORIN No. 61) in their second leaf stage. The wheat plants had been grown in square plastic pots (6 cm×6 cm). After the leaves were air-dried, they were inoculated with *Erysiphe graminis* f. sp *tritici* taken from wheat plants infected with wheat powdery mildew, by sprinkling. 8 days after the inoculation, the lesion degree of the wheat powdery mildew was examined. The protective values were calculated as were in Experiment Example 1.

The results revealed that Compound (1-1b) and Compound (1-2b) each showed a protective value of 90% or more.

INDUSTRIAL APPLICABILITY

Since the present invention has excellent antimicrobial properties against pathogenic microorganisms that cause plant diseases, the present invention is suitable as an active ingredient in a controlling agent capable of controlling plant diseases.

The invention claimed is:

1. A triazole compound represented by Formula (I):

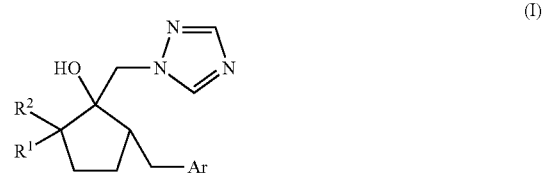

wherein $R^1$ represents a $C_1$-$C_6$ alkyl group; $R^2$ represents a $C_1$-$C_6$ haloalkyl group; and Ar represents a $C_6$-$C_{10}$ aromatic hydrocarbon group in which a hydrogen atom(s) may be substituted or a 5-10-membered aromatic heterocyclic group in which a hydrogen atom(s) may be substituted, the triazole compound being a compound in which —OH group, —$R^2$ group, and $CH_2$—Ar group are bonded in cis configuration with a cyclopentane ring, and the triazole compound being (−)-enantiomer.

2. The triazole compound as set forth in claim 1, represented by Formula (Ia):

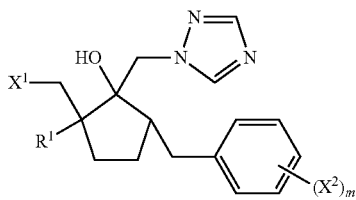

wherein $R^1$ represents a $C_1$-$C_6$ alkyl group; $X^1$ and $X^2$ independently represent a halogen atom; and m is 0 or 1,
the triazole compound being a compound in which —OH group, —CH$_2$—$X^1$ group, and substituted/unsubstituted benzyl group are bonded in cis configuration with a cyclopentane ring, and
the triazole compound being (−)-enantiomer.

3. The triazole compound as set forth in claim 2, wherein:
m is 1; and
$X^2$ represents a fluorine atom or a chlorine atom.

4. A triazole compound represented by Formula (I):

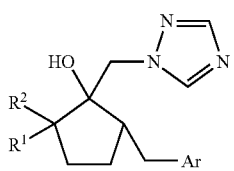

wherein $R^1$ represents a $C_1$-$C_6$ alkyl group; $R^2$ represents a $C_1$-$C_6$ haloalkyl group; and Ar represents a $C_6$-$C_{10}$ aromatic hydrocarbon group in which a hydrogen atom(s) may be substituted or 5-10-membered aromatic heterocyclic group in which a hydrogen atom(s) may be substituted,
the triazole compound being a compound in which —OH group, —$R^2$ group, and CH$_2$—Ar group are bonded in cis configuration with a cyclopentane ring, and
the triazole compound being (+)-enantiomer.

5. The triazole compound as set forth in claim 4, represented by Formula (Ia):

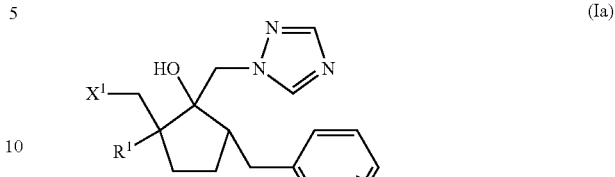

wherein $R^1$ represents a $C_1$-$C_6$ alkyl group; $X^1$ and $X^2$ independently represent a halogen atom; and m is 0 or 1,
the triazole compound being a compound in which —OH group, —CH$_2$—$X^1$ group, and substituted/unsubstituted benzyl group are bonded in cis configuration with a cyclopentane ring, and
the triazole compound being (+)-enantiomer.

6. The triazole compound as set forth in claim 5, wherein:
m is 1; and
$X^2$ represents a fluorine atom or a chlorine atom.

7. A microbial plant disease controlling agent comprising, as an active ingredient, a triazole compound as set forth in claim 1.

8. A microbial plant disease controlling agent comprising, as an active ingredient, a triazole compound as set forth in claim 4.

9. A method of controlling a microbial plant disease, comprising the step of: carrying out foliage treatment or non-foliage treatment with application of a microbial plant disease controlling agent as set forth in claim 7.

10. A seed which has been treated with a microbial plant disease controlling agent as set forth in claim 7.

11. A method of controlling a microbial plant disease, comprising the step of: carrying out foliage treatment or non-foliage treatment with application of a microbial plant disease controlling agent as set forth in claim 8.

* * * * *